United States Patent [19]

Shiokawa et al.

[11] Patent Number: 5,338,743
[45] Date of Patent: Aug. 16, 1994

[54] NEW USE OF THE ADENOSINE ANTAGONIST

[75] Inventors: Youichi Shiokawa, Ibaraki; Atsushi Akahane, Hyogo; Hirohito Katayama, Nishinomiya; Takafumi Mitsunaga, Ashiya, all of Japan

[73] Assignee: Fujisawa Pharmaceutical Co., Ltd., Osaka, Japan

[21] Appl. No.: 847,286

[22] Filed: Mar. 10, 1992

Related U.S. Application Data

[63] Continuation-in-part of Ser. No. 648,320, Jan. 29, 1991, abandoned, which is a continuation-in-part of Ser. No. 540,325, Jun. 19, 1990, Pat. No. 5,102,869, which is a continuation-in-part of Ser. No. 495,799, Mar. 19, 1990, Pat. No. 5,102,878, which is a continuation-in-part of Ser. No. 407,747, Sep. 15, 1989, Pat. No. 4,994,453, which is a continuation-in-part of Ser. No. 202,526, Jun. 6, 1988, Pat. No. 4,925,849, and Ser. No. 715,460, Jun. 14, 1991, Pat. No. 5,155,114, which is a continuation-in-part of Ser. No. 626,009, Dec. 12, 1990, abandoned, which is a continuation of Ser. No. 466,929, Jan. 18, 1990, Pat. No. 4,985,444.

[30] Foreign Application Priority Data

Jul. 9, 1991 [PH] Philippines ................ 42760

[51] Int. Cl.⁵ ............... A61K 31/33; A61K 31/395; A61K 31/55; A61K 31/54; A61K 31/535; A61K 31/53; A61K 31/50; A61K 31/495; A61K 31/505; A61K 31/435; A61K 31/44

[52] U.S. Cl. ................... 514/300; 514/183; 514/210; 514/211; 514/212; 514/218; 514/222.2; 514/222.5; 514/226.8; 514/227.5; 514/227.8; 514/228.8; 514/229.2; 514/231.2; 514/231.5; 514/231.8; 514/233.5; 514/235.8; 514/236.2; 514/236.5; 514/236.8; 514/241; 514/242; 514/247; 514/252; 514/255; 514/256; 514/277

[58] Field of Search ............ 514/300, 183, 210, 211, 514/212, 218, 222.2, 222.5, 226.8, 227.5, 227.8, 228.8, 229.2, 231.2, 231.5, 231.8, 233.5, 235.8, 236.2, 236.5, 236.8, 241, 242, 247, 252, 255, 256, 277

[56] References Cited

U.S. PATENT DOCUMENTS 4,483,987 11/1984 Wagner.

(List continued on next page.)

FOREIGN PATENT DOCUMENTS 0008391 3/1980 European Pat. Off. .

(List continued on next page.)

OTHER PUBLICATIONS

Chemical Abstracts, 180683x, vol. 94, Feb. 2, 1981, Grelan Pharmaceutical Co., Ltd., "Analgesic and Anti-Inflammatory Pharmaceuticals Containing Pyrazolo[1,5-a]Pyridine Derivatives".

(List continued on next page.)

Primary Examiner—Marianne M. Cintins
Assistant Examiner—Kimberly R. Jordan
Attorney, Agent, or Firm—Oblon, Spivak, McClelland, Maier & Neustadt

[57] ABSTRACT

The present method for the treatment of pancreatitis, which comprises administering an effective amount of a pyrazolopyridine compound of the following formula:

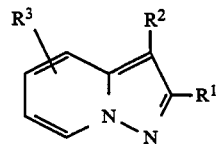

wherein
$R^1$ is lower alkyl, (substituted) aryl, or a heterocyclic group,
$R^2$ is a group of the formula

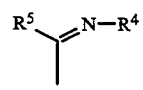

wherein $R^4$ is protected amino or hydroxy and $R^5$ is hydrogen or lower alkyl; cyano; a group of the formula —A—$R^6$, wherein $R^6$ is an acyl group, and A is (halogenated) lower aliphatic hydrocarbon group; amidated carboxy; an unsaturated heterocyclic group; or (protected) amino; and
$R^3$ is hydrogen, lower alkyl, lower alkoxy or halogen; or a pharmaceutically acceptable salt thereof, to a human being having pancreatitis or an animal having pancreatitis in need thereof.

15 Claims, No Drawings

U.S. PATENT DOCUMENTS

| | | | |
|---|---|---|---|
| 4,925,849 | 5/1990 | Shiokawa et al. | 514/300 |
| 4,985,444 | 1/1991 | Shiokawa et al. | 514/300 |
| 4,994,453 | 2/1991 | Shiokawa et al. | 514/212 |

FOREIGN PATENT DOCUMENTS

| | | |
|---|---|---|
| 0299209 | 1/1989 | European Pat. Off. . |
| 0383465A2 | 8/1990 | European Pat. Off. . |
| 0417790A2 | 3/1991 | European Pat. Off. . |
| 0423805A2 | 4/1991 | European Pat. Off. . |
| 0467248 | 1/1992 | European Pat. Off. . |
| 3536030 | 4/1987 | Fed. Rep. of Germany . |
| 60-13792 | 1/1985 | Japan . |
| 61-165386 | 7/1986 | Japan . |
| 2-221276 | 9/1990 | Japan . |
| 2-289518 | 11/1990 | Japan . |
| 3-204878 | 9/1991 | Japan . |
| 3-204879 | 9/1991 | Japan . |
| 3-204880 | 9/1991 | Japan . |
| WO90/12797 | 11/1990 | PCT Int'l Appl. . |

OTHER PUBLICATIONS

Chemical Abstracts, 115542g, vol. 95, May 9, 1981, Grelan Pharmaceutical Co., Ltd., "3-Carbamoyl-Pyrazolo[1,5-a]Pyridine".

Chemical Abstracts, 174822t, vol. 100, Dec. 22, 1983, R. Collins, et al., "Pyrazolopyridine Derivative".

Chemical Abstracts, 168459w, vol. 104, Aug. 7, 1985, S. Kakehi, et al., "Pyrazolo[1,5-a]Pyridine Derivatives".

Chemical Abstracts, 208877k, vol. 105, May 15, 1986, S. Kakehi, et al., "Pyrazolo[1,5-a]Pyridines".

Earl G. Burton et al, "Diol Metabolites of 7--Phenyl-1,2,4-Triazolo[2,3-C]Pyrimidines-5-Amines," U.S. Pat. No. 4,866,063, Issued Sep. 12, 1989 (As Obtained From The Lexis TM Database).

British Medical Journal, vol. 294, No. 6563, 1987, pp. 10-12, A. H. Watt, et al., "Reproduction Of Epigastric Pain Of Duodenal Ulceration By Adenosine".

NEW USE OF THE ADENOSINE ANTAGONIST

This application is a continuation-in-part of U.S. application Ser. No. 07/648,320, filed Jan. 29, 1991, now abandoned which in turn is a continuation-in-part of U.S. application Ser. No. 07/540,325, filed Jun. 19, 1990, now U.S. Pat. No. 5,102,869, which in turn is a continuation-in-part of U.S. application Ser. No. 07/495,799, filed Mar. 19, 1990, now U.S. Pat. No. 5,102,878, which in turn is a continuation-in-part of U.S. application Ser. No. 07/407,747, filed Sep. 15, 1989, now U.S. Pat. No. 4,994,453, which in turn is a continuation-in-part of U.S. application Ser. No. 07/202,526, filed Jun. 6, 1988, now U.S. Pat. No. 4,925,849; and a continuation-in-part of U.S. application Ser. No. 07/715,460, filed Jun. 14, 1991, now U.S. Pat. No. 5,185,114 which in turn is a continuation-in-part of U.S. application Ser. No. 07/626,009, filed Dec. 12, 1990, now abandoned, which in turn is a continuation application of U.S. application Ser. No. 07/466,929, filed Jan. 18, 1990, now U.S. Pat. No. 4,985,444.

The present invention relates to a new use of the adenosine antagonist or a pharmaceutically acceptable salt thereof.

More particularly, it relates to the utility of the adenosine antagonist for the prevention and/or the treatment of pancreatitis and/or ulcer such as peptic ulcer (e.g. gastric ulcer, duodenal ulcer, etc.) in a human being or an animal.

Accordingly, one object of the present invention is to provide a pharmaceutical composition for the prevention and/or the treatment of pancreatitis and/or ulcer such as peptic ulcer (e.g. gastric ulcer, duodenal ulcer, etc.) in a human being or an animal comprising, as an active ingredient, the adenosine antagonist or a pharmaceutically acceptable salt thereof.

Another object of the present invention is to provide a method for the prevention and/or the treatment of pancreatitis and/or ulcer such as peptic ulcer (e.g. gastric ulcer, duodenal ulcer, etc.) in a human being or an animal which comprises administering the adenosine antagonist to a human being or an animal.

A further object of the present invention is to provide a use of the adenosine antagonist for the manufacture of a medicament for the prevention and/or the treatment of pancreatitis and/or ulcer such as peptic ulcer (e.g. gastric ulcer, duodenal ulcer, etc.) in a human being or an animal.

An additional object of the present invention is to provide a use of the adenosine antagonist for preventing and/or treating pancreatitis and/or ulcer such as peptic ulcer (e.g. gastric ulcer, duodenal ulcer, etc.) in a human being or an animal.

The inventors of the present invention have found the adenosine antagonist and a pharmaceutically acceptable salt thereof are useful for the prevention and/or the treatment of pancreatitis and/or ulcer such as peptic ulcer (e.g. gastric ulcer, duodenal ulcer, etc.) in a human being or an animal and have completed the present invention.

The adenosine antagonist to be used in the present invention may include the novel and known ones which possess adenosine antagonistic action as their properties, preferably, ones having at least adenosine $A_1$ antagonistic action.

The preferred examples of said adenosine antagonist may include a pyrazolopyridine compound (I) of the following formula:

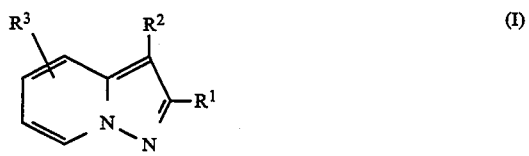

wherein
$R^1$ is lower alkyl, aryl which may have one or more suitable substituent(s) or a heterocyclic group,
$R^2$ is a group of the formula:

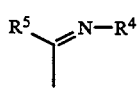

(wherein
$R^4$ is protected amino or hydroxy and
$R^5$ is hydrogen or lower alkyl);
cyano;
a group of the formula:

(wherein
$R^6$ is an acyl group, and
A is lower aliphatic hydrocarbon group which may have one or more suitable substituent(s));
amidated carboxy;
unsaturated heterocyclic group which may have one or more suitable substituent(s);
amino or protected amino; and
$R^3$ is hydrogen, lower alkyl, lower alkoxy or halogen, or a pharmaceutically acceptable salt thereof; a xanthine compound (II) of the following formula:

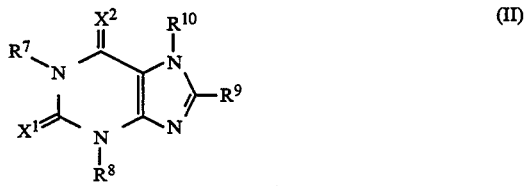

wherein
$R^7$, $R^8$ and $R^{10}$ are each hydrogen, lower aliphatic hydrocarbon group which may have one or more suitable substituent(s), higher alkyl which may have one or more suitable substituent(s) or ar(lower)alkyl which may have one or more suitable substituent(s),
$R^9$ is hydrogen; alicyclic group, aryl, heterocyclic group, alicyclic(lower)alkyl, ar(lower)alkyl or heterocyclic(lower)alkyl, each of which may have one or more suitable substituent(s); or a group of the formula:

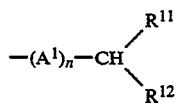

[wherein $R^{11}$ and $R^{12}$ are each alicyclic group which may have one or more suitable substituent(s) or aryl which may have one or more suitable substituent(s), $A^1$ is lower alkylene and n is 0 or 1], and $X^1$ and $X^2$ are each oxygen atom or sulfur atom, and a pharmaceutically acceptable salt thereof; and further, the compounds disclosed in the publications such as Japanese laid-open No. 3-204879, Japanese laid-open No. 3-204880, Japanese laid-open No. 2-289518, Japanese laid-open No. 3-204878, Japanese laid-open No. 61-165386, Japanese laid-open No. 60-13792, Japanese laid-open No. 2-221276, or the like; and the like.

In aforesaid pyrazolopyridine compound (I), the following compounds (Ia) and (Ib) are novel.

(1)

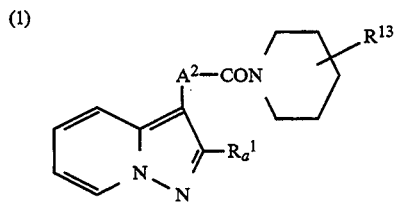
(Ia)

wherein $R_a^1$ is aryl, $R^{13}$ is acyl(lower)alkyl, and $A^2$ is lower alkenylene.

(2)

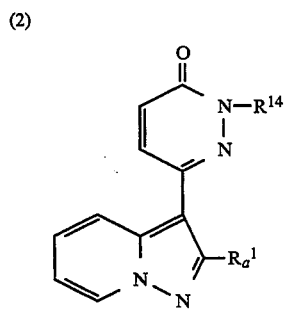
(Ib)

wherein $R_a^1$ is aryl, and $R^{14}$ is amino(lower)alkyl; lower alkylamino(lower)alkyl; carboxy(lower)alkylamino(lower)alkyl; protected carboxy(lower)alkylamino(lower)alkyl; lower alkylamino(lower)alkyl having hydroxy and aryloxy; protected amino(lower)alkyl; cyano(lower)alkyl; cyano(higher)alkyl; lower alkyl having heterocyclic group, in which heterocyclic group may have one or more suitable substituent(s); higher alkyl having heterocyclic group, in which heterocyclic group may have one or more suitable substituent(s); ar(lower)alkyl; lower alkenyl; or heterocyclic group which may have one or more suitable substituent(s).

The compounds (Ia) and (Ib) can be prepared, for example, according to the following procedures.

The Compound (Ia)

Process 1

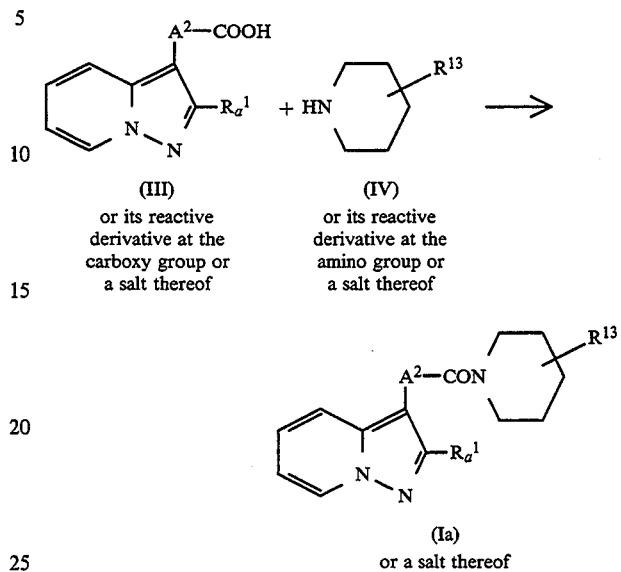

wherein $R_a^1$, $R^{13}$ and $A^2$ are each as defined above.

The Compound (Ib)

Process A

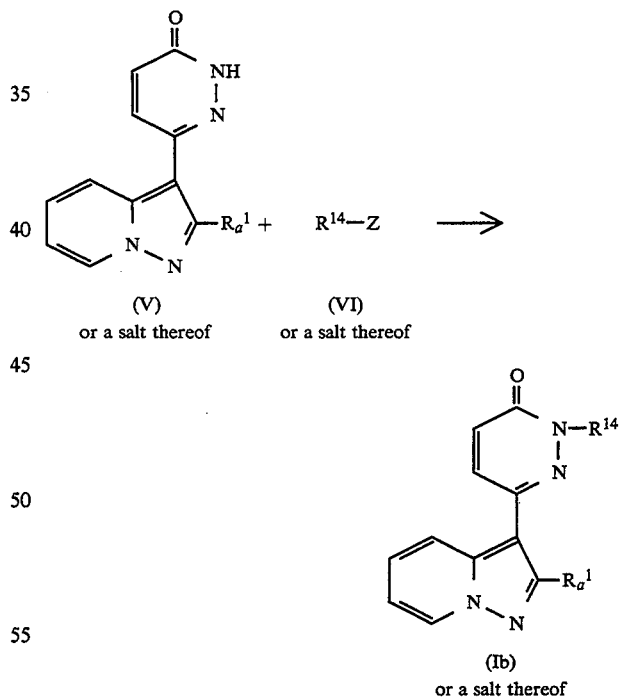

wherein $R_a^1$ and $R^{14}$ are each as defined above, and Z is a leaving group.

The reactions of aforesaid Processes 1 and A can be carried out according to the procedures disclosed in Preparations and Examples as mentioned later in the present specification.

The compounds (Ia) and (Ib) can be prepared according to the processes other than aforementioned Processes 1 and A illustrated also in Preparations and Examples disclosed later in the present specification.

The pyrazolopyridine compound (I) may include a novel compound other than the compounds (Ia) and (Ib), and said novel compound can be prepared from a known compound according to a similar manner to those of aforesaid Preparations and Examples or to a conventional manner in this field of the art.

The pyrazolopyridine compound (I) includes the known compounds which were disclosed in EP 0299209 and EP 0379979.

As for the xanthine compound (II), it includes the known compounds disclosed in the publications such as EP 0386675, EP 0415456, Japanese laid-open No. 2-247180, WO 90/12797 or the like.

The compound (II) may include the novel compounds, and in this case they can be prepared according to the similar procedures disclosed in the above-mentioned publications.

Suitable pharmaceutically acceptable salts of the adenosine antagonist to be used in the present invention are conventional ones and include a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), an organic acid salt (e.g. acetate, trifluoroacetate, maleate, tartrate, fumalate, methanesulfonate, benzenesulfonate, formate, toluenesulfonate, etc.), an inorganic acid salt (e.g. hydrochloride, hydrobromide, hydroiodide, sulfate, phosphate, etc.), a salt with an amino acid (e.g. arginine, aspartic acid, glutamic acid, etc.), and the like.

In the above and following descriptions of the present specification, suitable examples and illustrations of the various definitions which the present invention includes within the scope thereof are explained in detail as follows.

1. Pyrazolopyridine compound (I)

As for pyrazolopyridine compound (I), the various definitions are explained in the following.

The term "lower" is intended to mean 1 to 6 carbon atom(s) unless otherwise indicated.

The term "higher" is intended to mean 7 to 20 carbon atoms unless otherwise indicated.

Suitable "lower aliphatic hydrocarbon group" may include lower alkyl, lower alkenyl, lower alkynyl as explained below and the like.

Suitable "lower alkyl" may include straight or branched ones such as methyl, ethyl, propyl, isopropyl, butyl, t-butyl, pentyl, hexyl or the like, in which the preferred one may be ($C_1$–$C_4$) alkyl and the more preferred one may be methyl, ethyl, propyl and isopropyl.

Suitable "lower alkenyl" may include straight or branched ones such as vinyl, 1-methylvinyl, 2-methylvinyl, 1-propenyl, 2-propenyl, 1-butenyl, 2-methyl-1-propenyl, 1,3-butadienyl, 1-pentenyl, 4-pentenyl, 1-hexenyl, 1,4-hexadienyl, 5-hexenyl or the like, in which the preferred one may be ($C_2$–$C_4$)alkenyl and the more preferred one may be vinyl, 1-methylvinyl, 2-methylvinyl and 1,3-butadienyl.

Suitable "lower alkynyl" may include straight or branched ones such as ethynyl, 1-propynyl, 1-methylethynyl, 2-butynyl, 2-methyl-3-butynyl, 2-pentynyl, 1-hexynyl or the like, in which the preferred one may be ($C_2$–$C_4$)alkynyl and the more preferred one may be ethynyl.

Aforesaid "lower aliphatic hydrocarbon group" may have one or more (preferably one to three) suitable substituent(s) such as halogen (e.g. chloro, bromo, fluoro, iodo) or the like.

Suitable "protected amino" may include amino substituted with the conventional amino protective group such as lower alkylamino (e.g. methylamino, ethylamino, propylamino, butylamino, t-butylamino, pentylamino, hexylamino, etc.), di(lower) alkylamino (e.g. dimethylamino, diethylamino, N-ethylpropylamino, dibutylamino, N-(t-butyl) pentylamino, dihexylamino, etc.), acylamino explained below or the like.

Suitable "acylamino" may include ureido; lower alkanoylamino (e.g. formylamino, acetylamino, propionylamino, butyrylamino, isobutyrylamino, pivaloylamino, hexanoylamino, etc.), lower alkoxycarbonylamino (e.g. methoxycarbonylamino, ethoxycarbonylamino, propoxycarbonylamino, t-butoxycarbonylamino, pentyloxycarbonylamino, hexyloxycarbonylamino, etc.), lower alkoxycarbonyl(lower)alkanoylamino (e.g. methoxycarbonylacetylamino, ethoxycarbonylacetylamino, 2-(propoxycarbonyl)propionylamino 4-(t-butoxycarbonyl)butyrylamino, 2-(butoxycarbonylmethyl)propionylamino, 2-methyl-2-(pentyloxycarbonylmethyl)propionylamino, 6-hexyloxycarbonylhexanoylamino, etc.), lower alkanesulfonylamino (e.g. methanesulfonylamino, ethanesulfonylamino, propanesulfonylamino, butanesulfonylamino, t-butanesulfonylamino, pentanesulfonylamino, hexanesulfonylamino, etc.) and the like.

Said "lower alkanoylamino" may have suitable substituent(s) such as di(lower)alkylamino (e.g. dimethylamino, N-methyl-N-ethylamino, dipropylamino, di-t-butylamino, N-pentyl-N-hexylamino, etc.); cyclic amino group (e.g. piperidino, etc.) which may have lower alkyl; or the like, and suitable examples of said "lower alkanoylamino having suitable substituent(s)" may include lower alkanoylamino having di(lower)alkylamino [e.g. dimethylaminocarbonylamino, 2-dimethylaminoacetylamino, 2-(N-methyl-N-ethylamino)acetylamino, 2-dimethylaminopropionylamino, 3-dipropylaminobutyrylamino, 2-(di-t-butylamino)-2-methylpropionylamino, 2-dimethylaminomethyl-2-methylpropionylamino, 6-(N-pentyl-N-hexylamino)-hexanoylamino, etc.];

lower alkanoylamino having cyclic amino group which may have lower alkyl [e.g. piperidinocarbonylamino, 2-piperidinoacetylamino, 2-(2-methylpiperidino) acetylamino, 2-(2-ethylpiperidino)acetylamino, 2-piperidinopropionylamino, 3-(2-ethylpiperidino)butyrylamino, 2-(4-ethylpiperidino-2-methylpropionylamino, 2-piperidinomethyl-2-methylpropionylamino, 6-(3-propylpiperidino)hexanoylamino, etc.]; and the like.

In aforesaid "acylamino", the preferred one may be ureido, ($C_1$ –$C_4$) alkanoylamino, ($C_1$ –$C_4$)alkoxycarbonyl($C_1$–$C_4$)alkanoylamino, di($C_1$–$C_4$)alkylamino($C_1$–$C_4$)alkanoylamino, ($C_1$ –$C_4$)alkylpiperidino ($C_1$ –$C_4$)alkanoylamino, ($C_1$–$C_4$)alkoxycarbonylamino, ($C_1$–$C_4$)alkanesulfonylamino, ($C_1$–$C_4$)alkylamino and di($C_1$–$C_4$)alkylamino, in which the more preferred one may be ureido, acetylamino, 2-(ethoxycarbonyl)acetylamino, 2-dimethylaminoacetylamino, 2-(2-ethylpiperidino)acetylamino, methoxycarbonylamino, methanesulfonylamino, methylamino and dimethylamino.

Suitable "an acyl group" may include lower alkanoyl (e.g. formyl, acetyl, propionyl, butyryl, isobutyryl, pivaloyl, hexanoyl, etc.); carboxy; protected carboxy; and the like.

Suitable examples of aforesaid "protected carboxy" may be esterified carboxy, in which suitable esterified carboxy may include lower alkoxycarbonyl (e.g. methoxycarbonyl, ethoxycarbonyl, propoxycarbonyl, butoxycarbonyl, t-butoxycarbonyl, pentyloxycarbonyl, hexyloxycarbonyl, etc.) which may have N-containing heterocyclic group as explained below and the like;

amidated carboxy, in which suitable amidated carboxy may include N-(lower)alkylcarbamoyl (e.g. N-methylcarbamoyl, N-ethylcarbamoyl, N-isopropylcarbamoyl, N-butylcarbamoyl, N-pentylcarbamoyl, N-hexylcarbamoyl, etc.);

N-(higher)alkylcarbamoyl (e.g. N-heptylcarbamoyl, N-(2-methylheptyl)carbamoyl, N-nonylcarbamoyl, N-decanylcarbamoyl, N-tricyclo[3.3.1.1$^{3,7}$]decanylcarbamoyl, N-undecanylcarbamoyl, N-(bicyclo[4.3.2]undecanyl)carbamoyl, N-dodecanylcarbamoyl, N-tridecanylcarbamoyl, N-tetradecanylcarbamoyl, N-pentadecanylcarbamoyl, N-hexadecanylcarbamoyl, N-heptadecanylcarbamoyl, N-octadecanylcarbamoyl, N-nonadecanylcarbamoyl, N-icosanylcarbamoyl, etc.);

N,N-di(lower)alkylcarbamoyl [e.g. N,N-dimethylcarbamoyl, N,N-diethylcarbamoyl, N-methyl-N-ethylcarbamoyl, N,N-dipropylcarbamoyl, N,N-di(t-butyl)carbamoyl, N-pentyl-N-hexylcarbamoyl, etc.];

N-lower alkyl-N-ar(lower)alkylcarbamoyl (e.g. N-methyl-N-benzylcarbamoyl, etc.); a group of the formula:

—COR$_N$ (wherein R$_N$ is N-containing heterocyclic group which may have one or more suitable substituent(s), in which N-containing heterocyclic group R$_N$ may contain the other hetero atom(s) such as N, O or S in its ring.

Suitable "N-containing heterocyclic group" may include saturated or unsaturated, monocyclic or polycyclic heterocyclic group such as unsaturated 3 to 8-membered (more preferably 5 to 7-membered) heteromonocyclic group containing 1 to 4 nitrogen atom(s), for example, azepinyl (e.g. 1H-azepinyl, etc.) pyrrolyl, pyrrolinyl, imidazolyl, pyrazolyl, pyridyl and its N-oxide, dihydropyridyl, pyrimidinyl, pyrazinyl, pyridazinyl, triazolyl (e.g. 4H-1,2,4-triazolyl, 1H-1,2, 3-triazolyl, 2H-1,2,3- triazolyl, etc.), tetrazolyl (e.g. 1H-tetrazolyl, 2H-tetrazolyl, etc.) etc.;

saturated 3 to 8-membered(more preferably 5 to 7 membered)heteromonocyclic group containing 1 to 4 nitrogen atom(s), for example, perhydroazepinyl (e.g. perhydro-1H-azepinyl, etc.) pyrrolidinyl, imidazolidinyl, piperidino, piperazinyl, etc.;

unsaturated condensed heterocyclic group containing 1 to 4 nitrogen atom(s), for example, indolyl, isoindolyl, indolizinyl, benzimidazolyl, quinolyl, isoquinolyl, indazolyl, benzotriazolyl, etc.;

saturated condensed heterocyclic group containing 1 to 4 nitrogen atom(s), for example, 7-azabicyclo[2.2.1-]heptyl, 3-azabicyclo [3.2.2]nonanyl, etc.;

unsaturated 3 to 8-membered(more preferably 5 or 6-membered)heteromonocyclic group containing 1 to 2 oxygen atom(s) and 1 to 3 nitrogen atom(s), for example, oxazolyl, isoxazolyl, oxadiazolyl (e.g. 1,2,4-oxadiazolyl, 1,3,4-oxadiazolyl, 1,2,5-oxadiazolyl, etc.), etc.;

saturated 3 to 8-membered(more preferably 5 or 6-membered)heteromonocyclic group containing 1 to 2 oxygen atom(s) and 1 to 3 nitrogen atom(s), for example, morpholinyl, sydnonyl, etc.;

unsaturated condensed heterocyclic group containing 1 to 2 oxygen atom(s) and 1 to 3 nitrogen atom(s), for example, benzoxazolyl, benzoxadiazolyl, etc.;

unsaturated 3 to 8-membered(more preferably 5 or 6-membered)heteromonocyclic group containing 1 to 2 sulfur atom(s) and 1 to 3 nitrogen atom(s), for example, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.), dihydrothiazinyl, etc.;

saturated 3 to 8-membered (more preferably 5 or 6-membered) heteromonocyclic group containing 1 to 2 sulfur atom(s) and 1 to 3 nitrogen atom(s), for example, thiazolidinyl, etc.;

unsaturated condensed heterocyclic group containing 1 to 2 sulfur atom(s) and 1 to 3 nitrogen atom(s), for example, benzothiazolyl, benzothiadiazolyl, etc.; in which the preferred one may include saturated 3 to 8 membered heteromonocyclic group containing 1 to 4 nitrogen atom(s), saturated condensed heterocyclic group containing 1 to 4 nitrogen atom(s), and saturated 3 to 8 membered heteromonocyclic group containing 1 to 2 oxygen atom(s) and 1 to 3 nitrogen atom(s).

"N-containing heterocyclic group" thus defined may have one or more suitable substituent(s) such as lower alkyl as mentioned above; hydroxy(lower)alkyl (e.g, hydroxymethyl, 1-hydroxyethyl, 2-hydroxyethyl, 3-hydroxypropyl, 2-hydroxybutyl, 1-methyl-1-hydroxymethylethyl, 4-hydroxypentyl, 3-hydroxyhexyl, etc.); lower alkoxy(lower)alkyl (e.g. methoxymethyl, 2-methoxyethyl, 1-ethoxyethyl, 3-propoxypropyl, 2-(t-butoxy)butyl, 5-pentyloxypentyl, 3-hexyloxyhexyl, etc.); acyloxy(lower)alkyl such as lower alkanoyloxy(-lower)alkyl (e.g. acetoxymethyl, 1-acetoxyethyl, 2-acetoxyethyl, 2-propionyloxyethyl, 3-propionyloxypropyl, 2-butyryloxybutyl, 4-pivaloyloxypentyl, 6-hexanoyloxyhexyl, etc.) or the like; protected carboxy such as lower alkoxycarbonyl as mentioned above; carboxy; acyl(lower)alkyl such as lower alkanoyl(lower)alkyl (e.g. formylmethyl, 1-formylethyl, 2-acetylethyl, 2-formylpropyl, 3-propionylpropyl, 4-formylbutyl, 2-butyrylbutyl, 1-(formylmethyl)ethyl, 3-formylpentyl, 1-isobutyrylpentyl, 4-pivaloylpentyl, 2-formylhexyl, 6-hexanoylhexyl, etc.), carboxy(lower)alkyl (e.g. carboxymethyl, 1-carboxyethyl, 2-carboxypropyl, 1-(carboxymethyl)ethyl, 4-carboxybutyl, 3-carboxypentyl, 2-carboxyhexyl, etc.) or protected carboxy(lower)alkyl, in which the preferred "protected carboxy(lower)alkyl" may be esterified carboxy(lower)alkyl, the most preferred one may be lower alkoxycarbonyl(lower)alkyl (e.g. methoxycarbonylmethyl, 2-methoxycarbonylethyl, 1-ethoxycarbonylethyl, 2-propoxycarbonylpropyl, 1-(methoxycarbonylmethyl)ethyl, 4-t-butoxycarbonylbutyl, 3-pentyloxycarbonylpentyl, 2-hexyloxycarbonylhexyl, etc.); or the like.

In aforesaid "N-containing heterocyclic group which may have one or more suitable substituent(s)", the more preferred one may include piperidino which may have 1 to 4 suitable substituent(s) selected from a group consisting of ($C_1$–$C_4$)alkyl, hydroxy($C_1$–$C_4$)alkyl, ($C_1$–$C_4$)alkoxy($C_1$–$C_4$)alkyl, ($C_1$–$C_4$)alkanoyloxy($C_1$–$C_4$)alkyl, ($C_1$–$C_4$)alkoxycarbonyl, carboxy, ($C_1$–$C_4$)alkanoyl($C_1$–$C_4$)alkyl, carboxy($C_1$–$C_4$)alkyl and ($C_1$–$C_4$)alkoxycarbonyl($C_1$–$C_4$)alkyl (e.g. piperidino, 2-methylpiperidino, 2-ethylpiperidino, 3-ethylpiperidino, 4- ethylpiperidino, 2-propylpiperidino, 4-isopropylpiperidino, 2-butylpiperidino, 3-(t-butyl)piperidino, 4-pentylpiperidino, 2-hexylpiperidino, 2,2,6,6-tetramethylpiperidino, 2,2-dimethyl-6,6-diethylpiepridino, 2-hydroxymethylpiperidino, 3-hydroxymethylpiperidino, 2-(1-hydroxyethyl)piperidino, 2-(2-hydroxyethyl)piperidino, 3-(2-hydroxyethyl)piperidino, 4-(2-hydroxyethyl)piperidino, 2-(3-hydroxypropyl)piperidino, 3-(2-hydroxybutyl)piperidino, 2-(1-methyl-1-hydroxymethylethyl)piperidino, 4-(4-hydroxypentyl)piperidino, 2-(3-hydroxyhexyl)piperidino, 2-methoxymethylpiperidino, 2-(2-methoxyethyl)piperidino, 2-(1-ethoxyethyl)piperidino, 3-(3-propoxypropyl)piperidino, 4-{2-(t-butoxy)butyl}piperidino, 2-(5-pentyloxypentyl)piperidino, 3-(3-hexyloxyhexyl)piperidino, 2-acetoxymethylpiperidino, 3-(1-acetoxyethyl)piperidino, 2-(2-acetoxyethyl)piperidino, 3-(2-propionyloxyethyl)piperidino, 4-(3-propionyloxypropyl)piperidino, 2-(2-butyryloxybutyl)piperidino, 3-(4-pivaloyloxypentyl)piperidino, 2-(6-hexanoyloxyhexyl)piperidino, 2-methoxycarbonylpiperidino, 2-ethoxycarbonylpiperidino, 2-propoxycarbonylpiperidino, 3-butoxycarbonylpiperidino, 4-(t-butoxycarbonyl)piperidino, 2-pentyloxycarbonylpiperidino, 2-hexyloxycarbonylpiperidino, 2-carboxypiperidino, 3-carboxypiperidino, 4-carboxypiperidino, 2-(2-hydroxyethyl)-3-methylpiperidino, 2-(2-hydroxyethyl)-4-carboxypiperidino, 2-formylmethylpiperidino, 2-(1-formylethyl)piperidino, 3-(2-acetylethyl)piperidino, 4-(2-formylpropyl)piperidino, 2-(3-propionylpropyl)piperidino, 2-(4-formylbutyl)piperidino, 3-(2-butyrylbutyl)piperidino, 2-[1-(formylmethyl)ethyl]piperidino, 2-carboxymethylpiperidino, 2-(1-carboxyethyl)piperidino, 3-(2-carboxypropyl)piperidino, 4-[1-(carboxymethyl)ethyl]piperidino, 2-(4-carboxybutyl)piperidino, 2-methoxycarbonylmethylpiperidino, 2-(2-methoxycarbonylethyl)piperidino, 3-(1-ethoxycarbonylethyl)piperidino, 4-(2-propoxycarbonylpropyl)piperidino, 2-[1-(methoxycarbonylmethyl)ethyl]piperidino, 2-(4-t-butoxycarbonylbutyl)piperidino, etc.);

pyrrolidin-1-yl which may have $(C_1-C_4)$alkoxy$(C_1-C_4)$alkyl (e.g. pyrrolidin-1-yl, 2-methoxymethylpyrrolidin-1-yl, 2-(2-methoxyethyl)pyrrolidin-1-yl, 2-(1-ethoxyethyl)pyrrolidin-1-yl, 3-(3-propoxypropylpyrrolidin-1-yl, 3-{2-(t-butoxy)butyl}pyrrolidin-1-yl, 2-(5-pentyloxypentyl)pyrrolidin-1-yl, 2-(3-hexyloxyhexyl)pyrrolidin-1-yl, etc.);

perhydroazepin-1-yl (e.g. perhydro-1H-azepin-1-yl, etc.);

piperazin-1-yl which may have $(C_1-C_4)$alkyl (e.g. piperazin-1-yl, 2-methylpiperazin-1-yl, 3-methylpiperazin-1-yl, 4-methylpiperazin-1-yl, 2-ethylpiperazin-1-yl, 3-propylpiperazin-1-yl, 4-isopropylpiperazin-1-yl, 2-butylpiperazin-1-yl, 3-(t-butyl)piperazin-1-yl, 4-pentylpiperazin-1-yl, 4-hexylpiperazin-1-yl, etc.);

morpholino; 7-azabicyclo[2.2.1]heptan-7-yl; 3-azabicyclo[3.2.2]nonan-3-yl; and the like, and the most preferred one may include piperidino, 2-methylpiperidino, 2-ethylpiperidino, 3-ethylpiperidino, 4-ethylpiperidino, 2-propylpiperidino, 2,2,6,6-tetramethylpiperidino, 2-hydroxymethylpiperidino, 2-(2-hydroxyethyl)piperidino, 4-(2-hydroxyethyl)piperidino, 2-methoxymethylpiperidino, 2-(2-methoxyethyl)piperidino, 2-acetoxymethylpiperidino, 2-(2-acetoxyethyl)piperidino, 2-ethoxycarbonylpiperidino, 2-carboxypiperidino, pyrrolidin-1-yl, 2-methoxymethylpyrrolidin-1-yl, perhydro-1H-azepin-1-yl, 4-methylpiperazin-1-yl, morpholino, 7-azabicyclo[2.2.1]heptan-7-yl, 3-azabicyclo[3.2.2]nonan-3-yl, and the like.

Suitable "aryl" may include phenyl, naphthyl, indenyl, anthryl and the like and said "aryl" may have one or more suitable substituent(s) such as halogen (e.g. fluoro, chloro, bromo, iodo), lower alkoxy (e.g. methoxy, ethoxy, propoxy, t-butoxy, pentyloxy, hexyloxy, etc.), nitro, amino, protected amino as mentioned before or the like.

The preferred examples of "aryl which may have one or more suitable substituent(s)" may include phenyl which may have 1 to 3 suitable substituent(s) selected from a group consisting of halogen, $(C_1-C_4)$alkoxy, nitro, amino, $(C_1-C_4)$alkanoylamino, $(C_1-C_4)$alkoxycarbonylamino, $(C_1-C_4)$alkanesulfonylamino, $(C_1-C_4)$alkylamino and di$(C_1-C_4)$alkylamino, in which the more preferred one may be phenyl, phenyl having chloro, phenyl having methoxy, phenyl having nitro, phenyl having amino, phenyl having acetylamino, phenyl having methoxycarbonylamino, phenyl having methanesulfonylamino, phenyl having methylamino and phenyl having dimethylamino.

Suitable "a heterocyclic group" may include the ones as exemplified for "N-containing heterocyclic group" as mentioned above, unsaturated 3 to 8-membered (more preferably 5 or 6-membered) heteromonocyclic group containing an oxygen atom, for example, furyl, etc.;

unsaturated 3 to 8-membered (more preferably 5 or 6-membered)heteromonocyclic group containing an oxygen atom and 1 to 2 sulfur atom(s), for example, dihydrooxathiinyl, etc.;

unsaturated condensed heterocyclic group containing 1 to 2 sulfur atom(s), for example, benzothienyl, benzodithiinyl, etc.;

unsaturated condensed heterocyclic group containing an oxygen atom and 1 to 2 sulfur atom(s), for example, benzoxathiinyl, etc. and the like, in which the preferred one may be unsaturated 3 to 8 membered heteromonocyclic group containing 1 to 4 nitrogen atom(s), the more preferred one may be pyridyl and the most preferred one may be 2-pyridyl, 3-pyridyl and 4-pyridyl.

Suitable "lower alkenyl having halogen" may include 1-fluorovinyl, 1-bromovinyl, 1-chloro-2-methylvinyl, 1-bromo-1-propenyl, 2-chloro-2-propenyl, 1-iodo-1-butenyl, 1-bromo-2-methyl-1-propenyl, 3-bromo-1,3-butadienyl, 1-chloro-1-pentenyl, 4-chloro-4-pentenyl, 1-bromo-1-hexenyl and the like.

Suitable "lower alkoxy" may include methoxy, ethoxy, propoxy, isopropoxy, butoxy, t-butoxy, pentyloxy, hexyloxy and the like.

Suitable "halogen" may include fluoro, chloro, bromo and iodo.

Suitable "a leaving group" may include di(lower)alkylamino (e.g. dimethylamino, diethylamino, N-ethylpropylamino, dibutylamino, N-pentylhexylamino, etc.), lower alkoxy as mentioned above, halogen as mentioned above, lower alkylthio (e.g. methylthio, ethylthio, propylthio, butylthio, pentylthio, hexylthio, etc.) and the like.

Suitable "unsaturated heterocyclic group" in "unsaturated heterocyclic group which may have one or more suitable substituent(s)" may include unsaturated, monocyclic or polycyclic heterocyclic group containing at least one hetero atom such as nitrogen, oxygen, sulfur or the like.

Suitable examples of said "unsaturated heterocyclic group" may include:

unsaturated 3 to 8-membered (more preferably 5 to 7-membered) heteromonocyclic group containing 1 to 4 nitrogen atom(s), for example, azepinyl (e.g. 1H-azepinyl, etc.) pyrrolyl, pyrrolinyl, imidazolyl, pyrazolyl, pyridyl, dihydropyridyl (e.g. 1,2-dihydropyridyl, 1,4-dihydropyridyl, etc.), tetrahydropyridyl (e.g. 1,2,3,6-tetrahydropyridyl, etc.) pyrimidinyl, dihydropyrimidinyl (e.g. 1,2-dihydropyrimidinyl, etc.), pyrazinyl, pyridazinyl, dihydropyridazinyl (e.g. 2,3-dihydropyridazinyl, 1,4-dihydropyridazinyl, etc.), tetrahydropyridazinyl (e.g. 2,3,4,5-tetrahydropyridazinyl, etc.) triazolyl (e.g. 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), etc.;

unsaturated condensed heterocyclic group containing 1 to 4 nitrogen atom(s), for example, indolyl, isoindolyl, indolizinyl, benzimidazolyl, quinolyl, dihydroquinolyl (e.g. 2,3-dihydroquinolyl, etc.) isoquinolyl, indazolyl, benzotriazolyl, etc.;

unsaturated 3 to 8-membered (more preferably 5 or 6-membered) heteromonocyclic group containing 1 to 2 oxygen atom(s) and 1 to 3 nitrogen atom(s), for example, oxazolyl, isoxazolyl, dihydroisoxazolyl (e.g. 2,5-dihydroisoxazolyl, etc.) oxadiazolyl (e.g. 1,2,4-oxadiazolyl, 1,3,4-oxadiazolyl, 1,2,5-oxadiazolyl, etc.), etc.;

unsaturated condensed heterocyclic group containing 1 to 2 oxygen atom(s) and 1 to 3 nitrogen atom(s), for example, benzoxazolyl, benzoxadiazolyl, etc.;

unsaturated 3 to 8-membered (more preferably 5 or 6-membered)heteromonocyclic group containing 1 to 2 sulfur atom(s) and 1 to 3 nitrogen atom(s), for example, thiazolyl, dihydrothiazolyl (e.g. 2,3-dihydrothiazolyl, etc.) isothiazolyl, thiadiazolyl (e.g. 1,2,3-thiadiazolyl, 1,2,4-thiadiazolyl, 1,3,4-thiadiazolyl, 1,2,5-thiadiazolyl, etc.), dihydrothiazinyl, etc.;

unsaturated condensed heterocyclic group containing 1 to 2 sulfur atom(s) and 1 to 3 nitrogen atom(s), for example, benzothiazolyl, benzothiadiazolyl, (e.g. benzo[d][1,2,3]thiadiazolyl, etc.), imidazothiadiazolyl (e.g. 5H-imidazo[2,1-b][1,3,4]thiadiazolyl, etc.), etc.;

unsaturated 3 to 8-membered (more preferably 5 or 6-membered) heteromonocyclic group containing 1 to 2 sulfur atom(s), for example, thienyl, dihydrodithiinyl, etc.;

unsaturated 3 to 8-membered (more preferably 5 or 6-membered) heteromonocyclic group containing an oxygen atom, for example, furyl, etc.;

unsaturated 3 to 8-membered (more preferably 5 or 6-membered) heteromonocyclic group containing an oxygen atom and 1 to 2 sulfur atom(s), for example, dihydrooxathiinyl, etc.;

unsaturated condensed heterocyclic group containing 1 to 2 sulfur atom(s), for example, benzothienyl, benzodithiinyl, etc.;

unsaturated condensed heterocyclic group containing an oxygen atom and 1 to 2 sulfur atom(s) for example, benzoxathiinyl, etc. and the like, in which the preferred one may be unsaturated heterocyclic group containing at least one nitrogen atom as hetero atom, the more preferred one may be unsaturated 3 to 8-membered heteromonocyclic group containing 1 to 4 nitrogen atom(s) and unsaturated condensed heterocyclic group containing 1 to 2 sulfur atom(s) and 1 to 3 nitrogen atom(s), the much more preferred one may be pyridazinyl, dihydropyridazinyl, tetrahydropyridazinyl, pyrimidinyl, dihydropyrimidinyl, pyridyl, dihydropyridyl, tetrahydropyridyl, pyrazolyl and imidazothiadiazolyl, and the most preferred one may be pyridazinyl, 2,3-dihydropyridazinyl, 1,4-dihydropyridazinyl, 2,3,4,5-tetrahydropyridazinyl, pyrimidinyl, 1,2-dihydropyrimidinyl, pyridyl, 1,2-dihydropyridyl, 1,4-dihydropyridyl, 1,2,3,6-tetrahydropyridyl, pyrazolyl, and imidazo[2,1-b][1,3,4]thiadiazolyl.

Aforesaid "unsaturated heterocyclic group" may have one or more (preferably 1 to 4) suitable substituent(s) such as lower alkyl (e.g. methyl, ethyl, propyl, isopropyl, butyl, t-butyl, pentyl, hexyl, etc.) which may have one or more (preferably 1 to 4) suitable substituent(s) as explained below; carboxy(lower)alkenyl (e.g. 1-carboxyvinyl, 2-carboxyvinyl, 1-carboxy-2-propenyl, 3-carboxy-2-propenyl, 3-carboxy-2-butenyl, 4-carboxy-2-methyl-2-butenyl, 3-carboxy-1-hexenyl, etc.); amino; di(lower)alkylamino (e.g. dimethylamino, N-methylethylamino, dipropylamino, N-butyl-(2-methylbutyl)amino, N-pentylhexylamino, etc.); halogen (e.g. fluoro, chloro, bromo, iodo, etc.); lower alkoxy (e.g. methoxy, ethoxy, propoxy, isopropoxy, butoxy, t-butoxy, pentyloxy, hexyloxy, etc.); oxo; hydroxy; cyano; an acyl group as explained below; or the like.

Suitable "an acyl group" may include lower alkanoyl (e.g. formyl, acetyl, propionyl, butyryl, isobutyryl, pivaloyl, hexanoyl, etc.), carboxy, protected carboxy, and the like.

Suitable examples of aforesaid "protected carboxy" may be esterified carboxy, in which suitable esterified carboxy may include lower alkoxycarbonyl (e.g. methoxycarbonyl, ethoxycarbonyl, propoxycarbonyl, t-butoxycarbonyl, pentyloxycarbonyl, hexyloxycarbonyl, etc.) and the like;

amidated carboxy, in which suitable amidated carboxy may include carbamoyl, N,N-di(lower)alkylcarbamoyl wherein two lower alkyl groups may bond to each other to form 3 to 6-membered ring (e.g. N,N-dimethylcarbamoyl, N-methyl-N-ethylcarbamoyl, N,N-diethylcarbamoyl, N,N-dipropylcarbamoyl, N-butyl-N-t-butylcarbamoyl, N,N-dipentylcarbamoyl, N-pentyl-N-hexylcarbamoyl, 1-aziridinylcarbonyl, 1-azetidinylcarbonyl, 1-pyrrolidinylcarbonyl, piperidinocarbonyl, etc.) and the like; or the like.

Suitable examples of "suitable substituent(s)" of aforesaid "lower alkyl which may have one or more suitable substituent(s)" may include hydroxy, aforesaid halogen, aforesaid lower alkoxy, aforesaid an acyl group, and the like.

Suitable examples of said "lower alkyl having one or more suitable substituent(s)" may include lower alkyl having hydroxy and halogen (e.g. 1-hydroxy-1-chloromethyl, 1-hydroxy-2-chloroethyl, 2-hydroxy-3-fluoropropyl, 2-hydroxy-3,3,3-trichloropropyl, 3-bromo-4-hydroxy-4-iodobutyl, 1-chloro-2-hydroxy-4-fluoropentyl, 3,4-dihydroxy-6-chlorohexyl, etc);

hydroxy(lower)alkyl (e.g. hydroxymethyl, 2-hydroxyethyl, 2-hydroxypropyl, 3-hydroxypropyl, 1-hydroxy-1-methylethyl, 1-hydroxybutyl, 1-hydroxymethyl-1-methylethyl, 3-hydroxypentyl, 2-hydroxyhexyl, etc.);

lower alkoxy(lower)alkyl (e.g. methoxymethyl, ethoxymethyl, 2-ethoxyethyl, 1-propoxyethyl, 3-isopropoxypropyl, 2-butoxybutyl, 1-t-butoxymethyl-1-methylethyl, 5-pentyloxypentyl, hexyloxymethyl, 3-hexyloxyhexyl, etc.);

acyl(lower)alkyl, in which the preferred one may be carboxy(lower)alkyl (e.g. carboxymethyl, 2-carboxyethyl, 2-carboxypropyl, 3-carboxypropyl, 2-carboxy- 1-methylethyl, 4-carboxybutyl, 1-carboxymethyl-1-methylethyl, 3-carboxypentyl, 2-carboxyhexyl, etc.), and protected carboxy(lower)alkyl, in which the preferred one may be esterified carboxy(lower)alkyl and amidated carboxy(lower)alkyl, the more preferred one may be lower alkoxycarbonyl(lower)alkyl (e.g. methoxycarbonylmethyl, ethoxycarbonylmethyl, 2-methoxycarbonylethyl, 2-ethoxycarbonylethyl, 1-propoxycarbonylethyl, 3-ethoxycarbonylpropyl, 2-butoxycarbonylbutyl, 4-ethoxycarbonylbutyl, 1-t-butoxycarbonylmethyl-1-methylethyl, 5-pentyloxycarbonylpentyl, hexyloxycarbonylmethyl, 3-hexyloxycarbonylhexyl, etc.), carbamoyl(lower)alkyl (e.g. carbamoylmethyl, 2-carbamoylethyl, 3-carbamoylpropyl, 2-carbamoyl-1-methylethyl, 4-carbamoylbutyl, 1-carbamoylmethyl-1-methylethyl, 5-carbamoylpentyl, 3-carbamoylhexyl, etc.), N,N-di(lower)alkylcarbamoyl(lower)alkyl in which two lower alkyl groups on nitrogen atom may bond to each other to form 3 to 6-membered ring [e.g. N,N-dimethylcarbamoylmethyl, 2-(N,N-dimethylcarbamoyl)ethyl, 2-(N-methyl-N-ethylcarbamoyl)ethyl, 3-(N-methyl-N-ethylcarbamoyl)propyl, 2-(N,N-dipropylcarbamoyl)-1-methylethyl, 4-(N,N-dipropylcarbamoyl)butyl, 1-(N,N-dimethylcarbamoyl)-methyl-1-methylethyl, 5-(N-pentyl-N-hexylcarbamoyl)-pentyl, 3-(N-pentyl-N-hexyl)hexyl, (1-aziridinylcarbonyl)methyl, 2-(1-azetidinylcarbonyl)ethyl, 2-(piperidinocarbonyl)ethyl, 3-(1-pyrrolidinylcarbonyl)-propyl, 2-(1-piperidinocarbonyl)-1-methylethyl, 4-(1-azetidinylcarbonyl)butyl, 1-(1-aziridinylcarbonyl)methyl-1-methylethyl, 3-(1-pyrrolidinylcarbonyl)pentyl, 6-(piperidinocarbonyl)hexyl, etc.]; and the like.

The preferred substituent of "unsaturated heterocyclic group" may be lower alkyl, lower alkyl having hydroxy and halogen, hydroxy(lower)alkyl, lower alkoxy(lower)alkyl, carboxy(lower)alkyl, lower alkoxycarbonyl(lower)alkyl, carbamoyl(lower)alkyl, N,N-di(lower)alkylcarbamoyl(lower)alkyl wherein two lower alkyl groups on nitrogen atom may bond to each other to form 3 to 6-membered ring, carboxy(lower)alkenyl, di(lower)alkylamino, halogen, lower alkoxy, oxo, carboxy, lower alkoxycarbonyl, lower alkanoyl, amino, cyano and hydroxy, in which the more preferred one may be ($C_1$–$C_4$)alkyl, ($C_1$–$C_4$)alkyl having hydroxy and halogen, hydroxy($C_1$–$C_4$)alkyl, ($C_1$–$C_4$)alkoxy($C_1$–$C_4$)alkyl, carboxy($C_1$–$C_4$)alkyl, ($C_1$–$C_4$)alkoxycarbonyl($C_1$–$C_4$)alkyl, carbamoyl($C_1$–$C_4$)alkyl, N,N-di($C_1$–$C_4$)alkylcarbamoyl($C_1$–$C_4$)alkyl, piperidinocarbonyl($C_1$–$C_4$)alkyl, carboxy($C_2$–$C_4$)alkenyl, di($C_1$–$C_4$)alkylamino, halogen, ($C_1$–$C_4$)alkoxy, oxo, carboxy, ($C_1$–$C_4$)alkoxycarbonyl, ($C_1$–$C_4$)alkanoyl, amino, cyano and hydroxy, and the most preferred one may be methyl, propyl, 2-hydroxy-3,3,3-trichloropropyl, 2-hydroxyethyl, 3-hydroxypropyl, 2-ethoxyethyl, 2-carboxyethyl, 3-carboxypropyl, 4-carboxybutyl, methoxycarbonylmethyl, 2-methoxycarbonylethyl, 3-ethoxycarbonylpropyl, 4-ethoxycarbonylbutyl, 2-carbamoylethyl, 2-(N,N-dimethylcarbamoyl)ethyl, 2-(piperidinocarbonyl)ethyl, 2-carboxyvinyl, dimethylamino, chloro, methoxy, oxo, carboxy, ethoxycarbonyl, methoxycarbonyl, acetyl, amino, cyano and hydroxy.

Aforesaid "unsaturated heterocyclic group" in "unsaturated heterocyclic group which may have one or more suitable substituent(s)" may have one or more (preferably 1 to 4) substituent(s) explained below as its "one or more suitable substituent(s)" in addition to the ones mentioned above, that is, amino(lower)alkyl; lower alkylamino(lower)alkyl; carboxy(lower)alkylamino(lower)alkyl; protected carboxy(lower)alkylamino(lower)alkyl; lower alkylamino(lower)alkyl having hydroxy and aryloxy, protected amino(lower)alkyl; cyano(lower)alkyl; cyano(higher)alkyl; lower alkyl having heterocyclic group in which heterocyclic group may have one or more suitable substituent(s); higher alkyl having heterocyclic group, in which heterocyclic group may have one or more suitable substituent(s); ar(lower)alkyl; lower alkenyl; or heterocyclic group which may have one or more suitable substituent(s).

Suitable "amino(lower)alkyl" may include aminomethyl, 1-aminoethyl, 2-aminoethyl, 2-aminopropyl, 3-aminobutyl, 2-amino-1,1-dimethylethyl, 5-aminopentyl, 1-aminohexyl, and the like, in which the preferred one may be amino($C_1$–$C_4$)alkyl and the more preferred one may be 2-aminoethyl.

Suitable "lower alkylamino(lower)alkyl" may include mono- or di- (lower)alkylamino(lower)alkyl" such as methylaminomethyl, 2-(ethylamino)ethyl, 3-(propylamino)propyl, 2-(propylamino)butyl, 2-(t-butylamino)-1,1-dimethylethyl, 4-pentylaminopentyl, 6-hexylaminohexyl, dimethylaminomethyl, 2-dimethylaminoethyl, 1-(N-methylethylamino)ethyl, 1-dimethylaminopropyl, 2-diethylaminopropyl, 3-dimethylaminopropyl, 3-(N-propylbutylamino)butyl, 4-dimethylaminobutyl, 2-dibutylamino-1,1-dimethylethyl, 4-dipentylaminopentyl, 6-(N-pentylhexylamino)hexyl, or the like; and the like, in which the preferred one may be di(lower)alkylamino(lower)alkyl, the more preferred one may be di($C_1$–$C_4$)alkylamino($C_1$–$C_4$)alkyl and the most preferred one may be 2-dimethylaminoethyl, 3-dimethylaminopropyl and 4-dimethylaminobutyl.

Suitable "carboxy(lower)alkylamino(lower)alkyl" may include carboxymethylaminomethyl, 2-(carboxymethylamino)ethyl, 2-(1-carboxyethylamino)ethyl, 3-(2-carboxypropylamino)propyl, 2-(3-carboxypropylamino)butyl, 2-(2-carboxy-1,1-dimethylethylamino)-1,1-dimethylethyl, 4-(5-carboxypentylamino)pentyl, 6-(3-carboxyhexylamino)hexyl, and the like, in which the preferred one may be carboxy($C_1$–$C_4$)alkylamino($C_1$–$C_4$)alkyl and the most preferred one may be 2-(carboxymethylamino)ethyl.

Suitable "protected carboxy" in "protected carboxy(lower)alkylamino(lower)alkyl" may be an esterified carboxy group, or the like, and concrete examples of the ester moiety in said esterified carboxy group may be the ones such as lower alkyl ester [e.g. methyl ester, ethyl ester, propyl ester, isopropyl ester, butyl ester, isobutyl ester, tert-butyl ester, pentyl ester, hexyl ester, 1-cyclopropylethyl ester, etc.] which may have suitable substituent(s), for example, lower alkanoyloxy(lower)alkyl ester [e.g. acetoxymethyl ester, propionyloxymethyl ester, butyryloxymethyl ester, valeryloxymethyl ester, pivaloyloxymethyl ester, 1-acetoxyethyl ester, 1-propionyloxyethyl ester, pivaloyloxymethyl ester, 2-propionyloxyethyl ester, hexanoyloxymethyl ester, etc.], lower alkanesulfonyl(lower)alkyl ester [e.g. 2-mesylethyl ester, etc.] or mono(or di or tri)halo(lower)alkyl ester [e.g. 2-iodoethyl ester, 2,2,2-trichloroethyl ester, etc.]; lower alkenyl ester [e.g. vinyl ester, allyl ester, etc.]; lower alkynyl ester [e.g. ethynyl ester, propynyl ester, etc.]; ar(lower)alkyl ester which may have suitable substituent(s) [e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-tert-butylbenzyl ester, etc.]; aryl ester which may have suitable substituent(s) [e.g. phenyl ester, 4-chlorophenyl ester, tolyl ester, 4-tert-butylphenyl ester, xylyl ester, mesityl ester, cumenyl ester, etc.]; or the like.

Suitable example of "protected carboxy(lower)alkylamino(lower)alkyl" may be esterified carboxy(lower)alkylamino(lower)alkyl, in which the preferred one may be lower alkoxycarbonyl(lower)alkylamino(lower)alkyl such as methoxycarbonylmethylaminomethyl, 2-(ethoxycarbonylmethylamino)ethyl, 2-(1-ethoxycarbonylethylamino)ethyl, 3-(2-propoxycarbonylpropylamino)propyl, 2-(3-butoxycarbonylpropylamino)butyl, 2-(2-t-butoxycarbonyl-1,1-dimethylethylamino)-1,1-dimethylethyl, 4-(5-pentyloxycarbonylpentylamino)pentyl, 6-(3-hexyloxycarbonylhexylamino)hexyl, or the like; the more preferred one may be ($C_1$–$C_4$)alkoxycarbonyl($C_1$–$C_4$)alkylamino($C_1$–$C_4$)alkyl, and the most preferred one may be 2-(ethoxycarbonylmethylamino) ethyl.

Suitable "lower alkylamino (lower) alkyl having hydroxy and aryloxy" may be aforesaid "lower alkylamino(lower)alkyl" having "hydroxy" and "aryloxy" (e.g. phenoxy, tolyloxy, naphthyloxy, etc.) and suitable examples thereof may include 1-(1-naphthyloxy)-1-hydroxymethylaminomethyl, 2-(1-hydroxy-2-phenoxyethylamino)ethyl, 2-[2-hydroxy-3-(1-naphthyloxy)propylamino]ethyl, 2-[4-hydroxy-3-(p-tolyloxy)butylamino]propyl, 2-[4-hydroxy-1-(2-naphthyloxy)-butylamino]-1,1-dimethylethyl, 4-[1-hydroxy-5-(1-naphthyloxy)pentylamino]pentyl, 6-[2-hydroxy-4-(2-naphthyloxy)hexylamino]hexyl, in which the preferred one may be ($C_1$–$C_4$)alkylamino($C_1$–$C_4$)alkyl having hydroxy and naphthyloxy and the more preferred one may be 2-[2-hydroxy-3-(1-naphthyloxy)-propylamino]ethyl.

Suitable "protected amino(lower)alkyl" may be acylamino(lower)alkyl.

Suitable example of the acylamino may be lower alkanoylamino [e.g. formylamino, acetylamino, propionylamino, hexanoylamino, pivaloylamino, etc.], mono(or di or tri)halo(lower)alkanoylamino [e.g. chloroacetylamino, trifluoroacetylamino, etc.], lower alkoxycarbonylamino [e.g. methoxycarbonylamino, ethoxycarbonylamino, tert-butoxycarbonylamino, tert-pentyloxycarbonylamino, hexyloxycarbonylamino, etc.], mono(or di or tri)halo(lower)alkoxycarbonylamino [e.g. chloromethoxycarbonylamino, dichloroethoxycarbonylamino, trichloroethoxycarbonylamino, etc.], aroylamino [e.g. benzoylamino, toluoylamino, xyloylamino, naphthoylamino, etc.], ar(lower)alkanoylamino such as phenyl(lower)alkanoylamino [e.g. phenylacetylamino, phenylpropionylamino, etc.], aryloxycarbonylamino [e.g. phenoxycarbonylamino, naphthyloxycarbonylamino, etc.], aryloxy(lower)alkanoylamino such as phenoxy(lower)alkanoylamino [e.g. phenoxyacetylamino, phenoxypropionylamino, etc.], arylglyoxyloylamino [e.g. phenylglyoxyloylamino, naphthylglyoxyloylamino, etc.], ar(lower)alkoxycarbonylamino which may have suitable substituent(s) such as phenyl(lower)alkoxycarbonylamino which may have nitro or lower alkoxy [e.g. benzyloxycarbonylamino, phenethyloxycarbonylamino, p-nitrobenzyloxycarbonylamino, p-methoxybenzyloxycarbonylamino, etc.], thienylacetylamino, imidazolylacetylamino, furylacetylamino, tetrazolylacetylamino, thiazolylacetylamino, thiadiazolylacetylamino, thienylpropionylamino, thiadiazolylpropionylamino, lower alkylsulfonylamino [e.g. methylsulfonylamino, ethylsulfonylamino, propylsulfonylamino, isopropylsulfonylamino, pentylsulfonylamino, butylsulfonylamino, etc.], arylsulfonylamino [e.g. phenylsulfonylamino, tolylsulfonylamino, xylylsulfonylamino, naphthylsulfonylanlino, etc.], ar(lower)alkylsulfonylamino such as phenyl(lower)alkylsulfonylamino [e.g. benzylsulfonylamino phenethylsulfonylamino, benzhydrylsulfonylamino, etc.], imide [e.g. 1,2-cyclohexanedicarboximide, succinimide, phthalimide, etc.], and the like.

Preferred example of said "protected amino(lower)alkyl" may be imido(lower)alkyl such as phthalimidomethyl, 2-phthalimidoethyl, 1-(1,2-cyclohexanedicarboximido)ethyl, 2-succinimidopropyl, 3-phthalimidobutyl, 2-(1,2-cyclohexanedicarboximido)-1,1-dimethylethyl, 5-phthalimidopentyl, 1-phthalimidohexyl, or the like, the more preferred one may be imido($C_1$–$C_4$)alkyl and the most preferred one may be 2-phthalimidoethyl.

Suitable "cyano(lower)alkyl" may include cyanomethyl, 1-cyanoethyl, 2-cyanoethyl, 3-cyanopropyl, 2-cyanobutyl, 4-cyanobutyl, 2-cyano-1,1-dimethylethyl, 4-cyanopentyl, 5-cyanopentyl, 6-cyanohexyl and the like, in which the preferred one may be cyano($C_1$–$C_6$)alkyl and the most preferred one may be cyanomethyl, 2-cyanoethyl, 3-cyanopropyl, 4-cyanobutyl, 5-cyanopentyl and 6-cyanohexyl.

Suitable "cyano(higher)alkyl" may include 7-cyanoheptyl, 8-cyanooctyl, 4-cyanooctyl, 8-cyano-3-methylheptyl, 9-cyanononyl, 1-cyanononyl, 10-cyanodecyl, 8-cyanoundecyl, 12-cyanododecyl, 11-cyano-4-methylundecyl, 13-cyanotridecyl, 6-cyanotetradecyl, 15-cyanopentadecyl, 12-cyanohexadecyl, 17-cyanoheptadecyl, 4-cyanooctadecyl, 19-cyanononadecyl, 1-cyano-12-ethylheptadecyl, 20-cyanoicosyl, and the like, in which the preferred one may be cyano($C_7$–$C_{16}$)alkyl and the more preferred one may be 7-cyanoheptyl, 8-cyanooctyl, 9-cyanononyl, 10-cyanodecyl and 12-cyanododecyl.

Suitable "lower alkyl" may be a straight or branched one such as methyl, ethyl, propyl, isopropyl, butyl, t-butyl, pentyl, hexyl or the like.

Suitable "lower alkenyl" may be a straight or branched one such as vinyl, allyl, 2-butenyl, 2-methyl-2-propenyl, 4-pentenyl, 3-hexenyl, or the like, in which the preferred one may be ($C_2$–$C_4$)alkenyl and the more preferred one may be vinyl.

Suitable "lower alkyl" in "lower alkyl having heterocyclic group, in which heterocyclic group may have one or more suitable substituent(s)" can be referred to the ones as exemplified before, and the preferred one may be ($C_1$–$C_6$)alkyl and the most preferred one may be methyl, ethyl, propyl, butyl, pentyl and hexyl.

Suitable "higher alkyl" in "higher alkyl having heterocyclic group, in which heterocyclic group may have one or more suitable substituent(s)" may include heptyl, octyl, 3-methylheptyl, nonyl, 2,6-dimethylheptyl, decyl, undecyl, dodecyl, 4-methyldodecyl, tridecyl, tetradecyl, pentadecyl, hexadecyl, heptadecyl, octadecyl, nonadecyl, 12-ethylheptadecyl, icosyl and the like, in which the preferred one may be ($C_7$–$C_{16}$)alkyl, and the more preferred one may be heptyl, octyl, nonyl, decyl, and dodecyl.

Suitable "heterocyclic group" in "lower alkyl having heterocyclic group, in which heterocyclic group may have one or more suitable substituent(s)" and "higher alkyl having heterocyclic group, in which heterocyclic group may have one or more suitable substituent(s)" means saturated or unsaturated, monocyclic or polycyclic heterocyclic group containing at least one heteroatom such as an oxygen, sulfur, nitrogen atom and the like. And, especially preferably heterocyclic group may be heterocyclic group such as unsaturated 3 to 8-membered heteromonocyclic group containing 1 to 4 nitrogen atom(s), for example, pyrrolyl, pyrrolinyl, imidazolyl, pyrazolyl, pyridyl, and its N-oxide, pyrimidyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), dihydrotriazinyl (e.g., 4,5-dihydro-1,2,4-triazinyl, 2,5-dihydro-1,2,4-triazinyl, etc.), etc.; saturated 3 to 8-membered heteromonocyclic group containing 1 to 4 nitrogen atom(s), for example, pyrrolidinyl, imidazolidinyl, piperidyl (e.g. piperidino, etc.), piperazinyl, etc.; unsaturated condensed heterocyclic group containing 1 to 5 nitrogen atom(s), for example, indolyl, isoindolyl, indolizynyl, benzimidazolyl, quinolyl, isoquinolyl, indazolyl, benzotriazolyl, tetrazolopyridyl, tetrazolopyridazinyl (e.g., tetrazolo[1,5-b]pyridazinyl, etc.), dihydrotriazolopyridazinyl, etc.; unsaturated 3 to 8-membered heteromonocyclic group containing 1 to 2 oxygen atom(s) and 1 to 3 nitrogen atom(s), for example, oxazolyl, isoxazolyl, oxadiazolyl, (e.g., 1,2,4-oxadiazolyl, 1,3,4-oxadiazolyl, 1,2,5-oxadiazolyl, etc.), etc.; saturated 3 to 8-membered heteromonocyclic group containing 1 to 2 oxygen atom(s) and 1 to 3 nitrogen atom(s), for example, morpholinyl, oxazolidinyl (e.g. 1,3-oxazolidinyl, etc.), etc.; unsaturated condensed heterocyclic group containing 1 to 2 oxygen atom(s) and 1 to 3 nitrogen atom(s), for example, benzoxazolyl, benzoxadiazolyl, etc.; unsaturated 3 to 8-membered heteromonocyclic group containing 1 to 2 sulfur atom(s) and 1 to 3 nitrogen atom(s), for example, 1,3-thiazolyl, 1,2-thiazolyl, thiazolinyl, thiadiazolyl (e.g., 1,2,4-thiadiazolyl, 1,3,4-thiadiazolyl, 1,2,5-thiadiazolyl, 1,2,3-thiadiazolyl), etc.; saturated 3 to 8-membered heteromonocyclic group containing 1 to 2 sulfur atom(s) and 1 to 3 nitrogen atom(s), for example, thiazolidinyl, etc.; unsaturated 3 to 8-membered heteromonocyclic group containing a sulfur atom, for example, thienyl, etc.; unsaturated condensed heterocyclic group containing 1 to 2 sulfur atom(s) and 1 to 3 nitrogen atom(s), for example, benzothiazolyl, benzothiadiazolyl, etc.; unsaturated 3 to 8-membered heteromonocyclic group containing 1 to 2 oxygen atom(s), for example, furyl, pyranyl, dioxolyl, etc.; saturated 3 to 8-membered heteromonocyclic group containing 1 to 2 oxygen atom(s), for example, oxolanyl, tetrahydropyranyl (e.g. tetrahydro-2H-pyran-2-yl etc.), dioxolanyl, etc.; unsaturated condensed heterocyclic group containing 1 to 2 oxygen atom(s), for example, isobenzofuranyl, chromenyl (e.g. 2H-chromen-3-yl, etc.), dihydrochromenyl (e.g. 3,4-dihydro-2H-chromen-4-yl, etc.), etc.; and the like.

Preferred example of "heterocyclic group" in "lower alkyl having heterocyclic group, in which heterocyclic group may have one or more suitable substituent(s)" and "higher alkyl having heterocyclic group, in which heterocyclic group may have one or more suitable substituent(s)" may be unsaturated 3 to 8-membered heteromonocyclic group containing 1 to 4 nitrogen atom(s); saturated 3 to 8-membered heteromonocyclic group containing 1 to 4 nitrogen atom(s); saturated 3 to 8-membered heteromonocyclic group containing 1 to 2 oxygen atom(s) and 1 to 3 nitrogen atom(s); and saturated 3 to 8-membered heteromonocyclic group containing 1 to 2 oxygen atom(s); in which the preferred one may be pyridyl, tetrazolyl, piperidyl, piperazinyl, morpholinyl, oxazolidinyl and tetrahydropyranyl; and the more preferred one may be 4-pyridyl, 1H-tetrazol-5-yl, piperidino, 1-piperazinyl, morpholino, 1,3-oxazolidin-5-yl and tetrahydro-2H-pyran-2-yl.

"Heterocyclic group" thus explained may have one or more (preferably 1 to 3) suitable substituent(s) such as hydroxy(lower)alkyl (e.g. hydroxymethyl, 2-hydroxyethyl, 1-hydroxypropyl, 4-hydroxybutyl, 2-hydroxy-1,1-dimethylethyl, 3-hydroxypentyl, 6-hydroxyhexyl, etc.), aryl which may have lower alkoxy (e.g. phenyl, naphthyl, 2-methoxyphenyl, 2-methoxynaphthyl, 3-ethoxyphenyl, 4-propoxyphenyl, 2-butoxyphenyl, 5-propoxynaphthyl, 3-t-butoxyphenyl, 4-pentyloxyphenyl, 2-hexyloxyphenyl, etc.), oxo, or the like, in which preferred "suitable substituent(s)" may be hydroxy($C_1$–$C_4$)alkyl, phenyl having ($C_1$–$C_4$)alkoxy and oxo, and the more preferred one may be 2-hydroxyethyl, 2-methoxyphenyl and oxo.

Suitable "heterocyclic group" in "heterocyclic group which may have one or more suitable substituent(s)" can be referred to the ones exemplified for "heterocyclic group" of "lower alkyl having heterocyclic group, in which heterocyclic group may have one or more suitable substituent(s)" and "higher alkyl having heterocyclic group, in which heterocyclic group may have one or more suitable substituent(s)", and the preferred one may be unsaturated condensed heterocyclic group containing 1 to 2 oxygen atom(s), the more preferred one may be dihydrochromenyl, and the most preferred one may be 3,4-dihydro-2H-chromen-4-yl.

This "heterocyclic group" may have one or more (preferably 1 to 4) suitable substituent(s) such as aforesaid lower alkyl, hydroxy, cyano or the like, in which the preferred one may be ($C_1$–$C_4$)alkyl, hydroxy and cyano, and the most preferred one may be methyl, hydroxy and cyano.

Suitable "ar(lower)alkyl" may include mono- or di- or tri- phenyl(lower)alkyl (e.g. benzyl, phenethyl, 2-phenylpropyl, 4-phenylbutyl, 2-phenyl-1,1-dimethylethyl, 1-phenylpentyl, 6-phenylhexyl, benzhydryl, trityl, etc.) and the like, in which the preferred one may be phenyl($C_1$–$C_4$)alkyl and the most preferred one may be benzyl.

Suitable "N-containing heterocyclic group" in "N-containing heterocyclic group which may have one or more suitable substituent(s)" may be heterocyclic group having at least one nitrogen atom as its ring member among the aforesaid "heterocyclic group", and said "N-containing heterocyclic group" may have one or more (preferably 1 to 3) suitable substituent(s) such as aforesaid hydroxy(lower)alkyl, aforesaid aryl which may have lower alkoxy, oxo or the like.

Suitable "tetrazolyl(lower)alkyl" may be 1H-tetrazol-5-ylmethyl, 2-(1H-tetrazol-5-yl)ethyl, 3-(1H-tetrazol-5-yl)propyl, 4-(1H-tetrazol-5-yl)butyl, 2-(2H-tetrazol-2-yl)-1,1-dimethylethyl, 4-(1H-tetrazol-1-yl)pentyl, 5-(1H-tetrazol-5-yl)pentyl, 6-(1H-tetrazol-5-yl)hexyl, or the like, in which the preferred one may be tetrazolyl($C_1$–$C_6$)alkyl and the more preferred one may be (1H-tetrazol-5-yl)methyl, 2-(1H-tetrazol-5-yl)ethyl, 3-(1H-tetrazol-5-yl)propyl, 4-(1H-tetrazol-5-yl)butyl, 5-(1H-tetrazol-5-yl)pentyl and 6-(1H-tetrazol-5-yl)hexyl.

Suitable "tetrazolyl(higher)alkyl" may be 7-(1H-tetrazol-5-yl)heptyl, 8-(1H-tetrazol-5-yl)octyl, 4-(1H-tetrazol-1-yl)octyl, 8-(1H-tetrazol-5-yl)-3methylheptyl, 9-(1H-tetrazol-5-yl)nonyl, 1-(1H-tetrazol-1-yl)nonyl, 10-(1H-tetrazol-5-yl)decyl, 8-(1H-tetrazol-5-yl)undecyl, 12-(1H-tetrazol-5-yl)dodecyl, 11-(1H-tetrazol-5-yl)-4-methylundecyl, 13-(1H-tetrazol-5-yl)tridecyl, 6-(1H-tetrazol-5-yl)tetradecyl, 15-(1H-tetrazol-5-yl)pentadecyl, 12-(1H-tetrazol-5-yl)hexadecyl, 17-(1H-tetrazol-1-yl)heptadecyl, 4-(1H-tetrazol-5-yl)octadecyl, 19-(1H-tetrazol-5-yl)nonadecyl, 1-(1H-tetrazol-1-yl)-12-ethylheptadecyl, 20-(1H-tetrazol-5-yl)icosyl, or the like, in which the preferred one may be tetrazolyl($C_7$-$C_{16}$)alkyl and the more preferred one may be 7-(1H-tetrazol-5-yl)heptyl, 8-(1H-tetrazol-5-yl)octyl, 9-(1H-tetrazol-5-yl)nonyl, 10-(1H-tetrazol-5-yl)decyl and 12-(1H-tetrazol-5-yl)dodecyl.

2. Xanthine compound (II)

The xanthine compound (II) includes all the compounds disclosed in the publications, EP 0386675, EP 0415456, Japanese laid-open No. 2-247180 and WO 90/12797, and so, the various definitions of compound (II) are the ones which can contain all the groups of the compounds disclosed in aforesaid publications.

Accordingly, the following explanations of the definitions concern especially suitable ones.

Suitable "lower aliphatic hydrocarbon group" in "lower aliphatic hydrocarbon group which may have one or more suitable substituent(s)" may include lower alkyl, lower alkenyl and lower alkynyl, each as explained for pyrazolopyridine compound (I).

Said "lower aliphatic hydrocarbon group" may have one or more (preferably 1 to 3) suitable substituent(s) such as hydroxy, amino, halogen as explained for compound (I), aryl as explained for compound (I), or the like.

In aforesaid "lower aliphatic hydrocarbon group", the preferred one may be ($C_1$-$C_4$)alkyl, ($C_2$-$C_4$)alkenyl or ($C_2$-$C_4$)alkynyl, the more preferred one may be ($C_1$-$C_4$)alkyl and the most preferred one may be propyl.

Suitable "higher alkyl" in "higher alkyl which may have one or more suitable substituent(s)" can be referred to the ones as explained for the compound (I), and this "higher alkyl" may have one or more (preferably 1 to 3) suitable substituent(s) as exemplified for the ones of "lower aliphatic hydrocarbon group".

Suitable "ar(lower)alkyl" may be the ones as explained for compound (I).

Said "ar(lower)alkyl" may have one or more (preferably 1 to 3) suitable substituent(s) such as aforesaid lower alkyl, aforesaid halogen, hydroxy aforesaid lower alkoxy, or the like.

Suitable "alicyclic group" and "alicyclic" moiety in "alicyclic(lower)alkyl" may include cyclo($C_3$-$C_8$)alkyl such as cyclopropyl, cyclobutyl, cyclopentyl, cyclohexyl, cycloheptyl, cyclooctyl or the like in which the preferred one may be cyclo ($C_3$-$C_6$) alkyl; ($C_7$-$C_{12}$)bicycloalkyl or ($C_7$-$C_{12}$)bicycloalkenyl, in which the preferred one may be a group of the formula:

(wherein is a single or a double bond), a group of the formula:

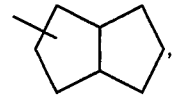

or the like; ($C_7$-$C_{12}$) tricycloalkyl, in which the preferred one may be a group of the formula:

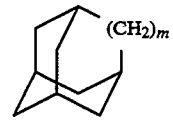

(wherein m is 0 or 1), or the like; and the like.

Suitable "heterocyclic group" and "heterocyclic" moiety in "heterocyclic(lower)alkyl" can be referred to the ones as illustrated for "a heterocyclic group" in compound (I).

Suitable "aryl" can be referred to the ones as exemplified for the compound (I).

Suitable "lower alkyl" moiety in "alicyclic(lower)alkyl" and "heterocyclic(lower)alkyl" can be referred to the ones as illustrated for "lower alkyl" before.

As for $R^9$, each of alicyclic group, aryl heterocyclic group, alicyclic(lower)alkyl, ar(lower)alkyl and heterocyclic(lower)alkyl may have one or more (preferably 1 to 3) suitable substituent(s) such as oxo, hydroxy, amino, aforesaid lower alkyl, carboxy, protected carboxy as explained for compound (I), or the like.

As for $R^{11}$ and $R^{12}$, "alicyclic group" and "aryl" may have one or more (preferably 1 to 3) suitable substituent(s) such as aforesaid lower alkyl, hydroxy, lower alkoxy as explained for compound (I), aforesaid halogen, amino, nitro or the like.

Suitable "lower alkylene" may include methylene, ethylene, 1-methyl-ethylene, trimethylene, tetramethylene, pentamethylene, hexamethylene or the like, in which the preferred one may be ($C_1$-$C_4$)alkylene.

The preferred embodiments of the groups of xanthine compound (II) are as follows.

The preferred $R^7$ and $R^8$ are each lower alkyl, the more preferred one are each ($C_1$-$C_4$)alkyl and the most preferred one are each propyl.

The preferred $R^9$ is cyclo($C_3$-$C_8$)alkyl which may have oxo; ($C_7$-$C_{12}$)tricycloalkyl and a group of the formula:

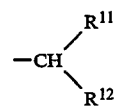

[wherein $R^{11}$ and $R^{12}$ are each cyclo($C_3$-$C_8$)alkyl], the more preferred one is cyclo($C_3$-$C_6$)alkyl which may have oxo; a group of the formula:

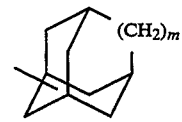

(wherein m is as defined above) and a group of the formula:

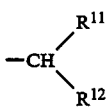

[wherein $R^{11}$ and $R^{12}$ are each cyclo($C_3$–$C_6$)alkyl]; and the most preferred one is cyclopentyl which may have oxo, a group of the formula:

and a group of the formula:

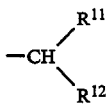

(wherein $R^{11}$ and $R^{12}$ are each cyclopropyl).

The preferred $R^{10}$ is hydrogen.

The preferred $X^1$ and $X^2$ are each oxygen atom.

The pharmaceutical composition of the present invention can be used in the form of a pharmaceutical preparation, for example, in solid, semisolid or liquid form, which contains the adenosine antagonist or a pharmaceutically acceptable salt thereof, as an active ingredient in admixture with an organic or inorganic carrier or excipient suitable for rectal, pulmonary (nasal or buccal inhalation), nasal, ocular, external (topical), oral or parenteral (including subcutaneous, intravenous and intramuscular) administrations or insufflation.

The active ingredient may be compounded, for example, with the usual non-toxic, pharmaceutically acceptable carriers for tablets, pellets, troches, capsules, suppositories, creams, ointments, aerosols, powders for insufflation, solutions, emulsions, suspensions, and any other form suitable for use. And, if necessary, in addition, auxiliary, stabilizing, thickening and coloring agents and perfumes may be used.

The adenosine antagonist or a pharmaceutically acceptable salt thereof is/are included in the pharmaceutical composition in an amount sufficient to produce the desired effect upon the process or condition of the diseases.

The pharmaceutical composition of the present invention can be manufactured by the conventional method in this field of the art. If necessary, the technique generally used in this field of the art for improving the bioavailability of a drug can be applied to the pharmaceutical composition of the present invention.

For applying the composition to a human being or an animal, it is preferable to apply it by intravenous (including i.v. infusion), intramuscular, pulmonary, or oral administration, or insufflation.

While the dosage of therapeutically effective amount of the adenosine antagonist varies from and also depends upon the age and condition of each individual patient to be treated, in the case of intravenous administration, a daily dose of 0.01–100 mg of the adenosine antagonist per kg weight of a human being or an animal, in the case of intramuscular administration, a daily dose of 0.01–100 mg of the adenosine antagonist per kg weight of a human being or an animal, in case of oral administration, a daily dose of 0.01–200 mg of the adenosine antagonist per kg weight of a human being or an animal is generally given for the prevention and/or the treatment of pancreatitis and/or ulcer in a human being or an animal.

In order to show the usefulness of the adenosine antagonist to be used in the present invention for the prevention and/or the treatment of pancreatitis and/or ulcer in a human being or an animal, the pharmacological test data of the representative compounds thereof are shown in the following.

Test Compounds (1) (2R)-1-[3-(2-Phenylpyrazolo[1,5-a]pyridin-3-yl)-acryloyl]-2-(2-hydroxyethyl)piperidine (trans isomer) [the compound of Example 22 of EP 0299209, hereinafter referred to as Test Compound (1)]

(2) 3-[2-(3-Carboxypropyl)-3-oxo-2,3-dihydropyridazin-6-yl]-2-phenylpyrazolo[1,5-a]pyridine [the compound of Example 36 of EP 0379979, hereinafter referred to as Test Compound (2)]

(3) (2R)-1-[3-(2-Phenylpyrazolo[1,5-a]pyridin-3-yl)-acryloyl]-2-(carboxymethyl)piperidine (trans isomer) [the compound of Example 79 of the present specification, hereinafter referred to as Test Compound (3)]

(4) 8-(Noradamantan-3-yl)-1,3-dipropylxanthine [the compound of Example 10 of EP 0415456, hereinafter referred to as Test Compound (4)]

(5) 8-Cyclopentyl-1,3-dipropylxanthine [the compound known as PD 116948, commercially available, hereinafter referred to as Test Compound (5)]

Test Methods and Results

Test 1. Effect on ischemia induced gastric ulcer

[I] Test Method

Male Sprague-Dawley rats (9 or 10 rats for one group) weighing 230 to 270 g were fasted for 24 hours but allowed free access to water ad libitum.

Under ether anesthesia, the abdomen was incised and the left gastric artery was ligated. After closing the abdomen, animals were maintained on regular feed with water ad libitum. The test compound (1) (10 mg/kg/5 ml) for the test group or vehicle (0.1% methyl cellulose, 5 ml/kg) for the control group was given orally twice a day (9:00 a.m. and 5:00 p.m.) from the first day after the operation for 3 consecutive days. On the fourth day after the operation, the test compound (for the test group) or vehicle (for the control group) was given at 9:00 a.m. and animals were killed at 5:00 p.m. The stomach was examined for ulcers.

Ulcer index was expressed as lesion area (mean±standard error).

|  | [II] Test Results | |
|---|---|---|
|  | ulcer index (mm$^2$) | inhibition (%) |
| control group | 26.2 ±6.0 | — |
| test group | 14.2 ±4.0 | 45.8 |

Test 2. Effect on serum amylase increment induced by caerulein administration with water immersion restraint stress in rats

[I] Test Method

Male Sprague-Dawley rats (6 rats for one group) weighing 210 to 240 g were fasted for 24 hours but allowed free access to water ad libitum. Immediately after caerulein administration (50 μg/kg/2 ml s.c.), rats were placed in restraint cages and immersed in water at 23° C. for 7 hours. The animals were killed and blood sample was collected from femoral blood vessels. Serum amylase was measured using Neo-Amylase Test "DAIICHI" (trademark, prepared by DAIICHI KAGAKU YAKUHIN). The test compound (1) (1 mg/kg/5 ml) for the test group or vehicle (0.1% methyl cellulose, 5 ml/kg) for the control group was given orally 30 minutes before caerulein administration.

Serum amylase concentration was expressed as mean±standard error.

[II] Test Results

|  | serum amylase ($10^3$ IU/L) |
|---|---|
| control group | 22.5 ± 3.3 |
| test group | 13.8 ± 1.0 |

Test 3. Effect on CHA($N^6$-cyclohexyladenosine)-induced pancreatitis

Male Sprague-Dawley rats, weighing 245–260 g, were deprived of food but allowed free access to water for 24 hours CHA was given orally at a dose of 3.2 mg/kg. After 24 hours, animals were killed and blood samples were collected. Subsequently, the blood serum was prepared and amylase concentration was determined. The test compounds (1) to (5) (10 mg/kg) or vehicle (to control group) was given orally 30 minutes before CHA administration. In Normal group, vehicle was given instead of CHA.

| Test Compound | N | serum amylase ($10^3$ IU/l) | inhibition % |
|---|---|---|---|
| Normal | 5 | 4.1 ± 0.2 | — |
| Control | 5 | 28.3 ± 10.0 | — |
| (1) | 5 | 11.5 ± 5.8 | 69.4 |
| (2) | 5 | 4.2 ± 0.3 | 99.6 |
| (3) | 5 | 5.9 ± 1.0 | 92.6 |
| (4) | 5 | 4.7 ± 0.4 | 97.5 |
| (5) | 5 | 3.9 ± 0.1 | 100 |

Test 4. Effect on CHA(N6-cyclohexyladenosine)-induced gastric ulcer

Male Sprague-Dawley rats, weighing 225–259 g, were deprived of food but allowed free access to water for 24 hours. CHA was given subcutaneously at a dose of 1 mg/kg. After 7 hours, animals were killed and stomachs were removed. Subsequently, the stomachs were inflated by injecting 12 ml of 2% formalin to fix the inner layer of gastric walls. Ten minutes later, they were incised along the greater curvature and examined for lesions. Test Compounds (1) to (5) (10 mg/kg) or vehicle (to control group) was given orally 30 minutes before CHA administration.

| Test Compound | N | ulcer index (mm$^2$) | inhibition % |
|---|---|---|---|
| Control | 7 | 65.0 ± 18.4 | — |
| (1) | 7 | 0.4 ± 0.4 | 99.4 |
| (2) | 7 | 1.9 ± 1.9 | 97.1 |
| (3) | 7 | 0.1 ± 0.1 | 99.8 |
| (4) | 7 | 0 ± 0 | 100 |
| (5) | 7 | 0.3 ± 0.3 | 99.5 |

In the following, the preparations of the novel pyrazolopyridine compounds (Ia) and (Ib) are explained by Preparations and Examples.

Preparation 1

A mixture of 3,6-dichloropyridazine (50 g), sodium benzenesulfinate dihydrate (100 g), benzyltrimethylammonium chloride (62.3 g), and 1,4-dioxane (335 ml) was stirred for 3 hours at 100° C. After being cooled to room temperature, aqueous solution of sodium hydroxide (510 ml) was added to the mixture, and the mixture was stirred for 0.5 hour at 100° C. The reaction mixture was cooled in a water bath and acidified with 36% hydrochloric acid (35 ml). The precipitate formed was collected, washed well with water, and dried to give 6-phenylsulfonyl-3-oxo-2,3-dihydropyridazine (54.7 g).

mp: 189°–191° C.

IR (Nujol): 1680, 1650, 1370, 1160 cm$^{-1}$

NMR (DMSO-d$_6$, δ): 7.12 (1H, d, J=10Hz), 7.6–7.9 (3H, m), 7.9–8.1 (3H, m) 13.85 (1H, broad s)

MASS m/z: 236

Anal. Calcd. for $C_{10}H_8N_2O_3S$: C 50.84, H 3.41, N 11.86, S 13.57 (%) Found: C 51.10, H 3.33, N 11.70, S 13.23 (%)

Preparation 2

To stirring phosphorous oxychloride (87 ml) at 80° C. was added four 2.0 g portions of 6-phenylsulfonyl-3-oxo-2,3-dihydropyridazine every 30 minutes. After additional two 1.0 g portions were added with stirring, the reaction mixture was slowly poured into ice-water over 1 hour to form the precipitate, which was collected, washed well with water, and dried to give 6-chloro-3-phenylsulfonylpyridazine (8.4 g).

An analytical sample was prepared by recrystallization from a mixture of diisopropyl ether and acetone (3:1).

mp: 142°–144° C.

IR (Nujol): 3100, 3050, 1580, 1540, 1370, 1180 cm$^{-1}$

NMR (CDCl$_3$, δ): 7.5–7.7 (3H, m], 7.74 (1H, d, J=9Hz), 8.0–8–2 (2H, m), 8.25 (1H, d, J=9Hz)

MASS m/z: 192 (M$^+$ - 62), 190 (M$^+$ - 64), 155

Anal. Calcd. for $C_{10}H_7ClN_2O_2S$: C 47.16, H 2.77, N 11.00, S 12.59 (%) Found: C 47.09, H 2.65, N 10.71, S 12.12 (%)

Preparation 3

To a solution of 6-chloro-3-phenylsulfonylpyridazine (8.4 g) bis(triphenylphosphine)palladium(II) chloride (98%; 0.24 g), copper(I) iodide (95%; 63 mg), and triethylamine (9.2 ml) in N,N-dimethylformamide (84 ml) was added phenylacetylene (4.7 ml), and the mixture was stirred for 0.5 hour at 80° C. After being cooled to room temperature, water (168 ml) was added to the reaction mixture. The precipitate formed was collected, washed with water, and dried. Recrystallization of the crude product from a mixture of diisopropyl ether and acetone (2:1) gave 6-(2-phenylethynyl)-3-phenylsulfonylpyridazine (5.5 g). After the mother liquor was concentrated in vacuo, the residue was triturated with acetone. The precipitate was collected and dried to give a second crop of the pure material (2.0 g).

mp: 179°-181° C.

IR (Nujol): 2200, 1370, 1180 cm$^{-1}$

NMR (CDCl$_3$, δ): 7.3-7.5 (3H, m), 7.5-7.7 (5H, m), 7.81 (1H, d, J=9Hz), 8.1-8.2 (2H, m), 8.25 (1H, d, J=9Hz)

MASS m/z: 256 (M$^+$ - 64)

Anal. Calcd. for C$_{18}$H$_{12}$N$_2$O$_2$S: C 67.48, H 3.78, N 8.74, S 10.00 (%) Found: C 67.53, H 3.69, N 8.23, S 9.71 (%)

Preparation 4

A two-phase mixture of 6-(2-phenylethynyl)-3-phenylsulfonylpyridazine (23.3 g), 1-aminopyridinium iodide (90%; 26.9 g), sodium hydroxide (11.6 g), and benzyltrimethylammonium chloride (1.35 g) in a mixture of methylene chloride (233 ml) and water (233 ml) was stirred for 2 hours at room temperature. Water (233 ml) was added to the reaction mixture, and the mixture was acidified with 36% hydrochloric acid (20 ml). The organic layer was separated, washed twice with water and once with sodium chloride aqueous solution, dried over anhydrous magnesium sulfate, and concentrated. The residue was washed with hot ethanol (300 ml) to give 3-(3-phenylsulfonylpyridazin-6-yl)-2-phenylpyrazolo[1,5-a]pyridine (20.8 g). An analytical sample was prepared by recrystallization from ethyl acetate.

mp: 192°-194° C.

IR (Nujol): 1620, 1560, 1370, 1180 cm$^{-1}$

NMR (CDCl$_3$, δ): 6.9-7.1 (1H, m), 7.3-7.5 (1H, m), 7.36 (1H, d, J=9Hz), 7.5-7.9 (8H, m), 7.93 (1H, d, J=9Hz), 8.1-8.2 (2H, m), 8.5-8.6 (2H, m)

MASS m/z: 412, 411 (M$^+$ - 1)

Anal. Calcd. for C$_{23}$H$_{16}$N$_4$O$_2$S: C 66.98, H 3.91, N 13.58, S 7.77 (%) Found: C 67.31, H 3.83, N 13.34, S 7.95 (%)

Preparation 5

A mixture of 3-(3-phenylsulfonylpyridazin-6-yl)-2-phenylpyrazolo[1,5-a]pyridine (20.0 g), sodium hydroxide solution (80 ml; containing 7.8 g of sodium hydroxide), and 1,4-dioxane (40 ml) was stirred for 2 hours under reflux. After being cooled to room temperature, the reaction mixture was acidified with 36% hydrochloric acid (15 ml). The precipitate formed was collected, washed with three 25 ml portions of water, and dried to give 3-(3-oxo-2,3-dihydropyridazin-6-yl)-2-phenylpyrazolo[1,5-a]pyridine (16.0 g). An analytical sample was prepared by recrystallization from ethyl acetate.

mp: 229°-230° C.

IR (Nujol): 1680, 1630 cm$^{-1}$

NMR (DSMO-d$_6$, δ): 6.84 (1H, d, J=10Hz), 7.12 (1H, d, J=10Hz), 7.0-7.1 (1H, m), 7.3-7.7 (6H, m), 7.86 (1H, broad d, J=9Hz), 8.82 (1H, broad d, J=7Hz), 13.19 (1H, broad s)

MASS m/z: 288, 287 (M$^+$ - 1)

Anal. Calcd. for C$_{17}$H$_{12}$N$_4$O: C 70.82, H 4.20, N 19.43 (%) Found: C 70.93, H 4.18, N 19.38 (%)

Preparation 6

To an ice-cooled solution of 3-(3-oxo-2,3-dihydropyridazin-6-yl)-2-phenylpyrazolo[1,5-a]pyridine (2.0 g) in N,N-dimethylformamide (20 ml) was added portionwise sodium hydride (60% dispersion in mineral oil; 0.31 g). After addition was finished, the mixture was stirred for 15 minutes in an ice-bath. To this mixture was added 4-chlorobutyl acetate (1.1 g), and the reaction mixture was stirred for 24 hours at room temperature, and then for 36 hours at 70° C. After being cooled to room temperature, the reaction mixture was concentrated. The residue was partitioned between ethyl acetate and water.

The organic layer was separated and the aqueous layer was extracted twice with ethyl acetate. The combined organic layers were washed with water and sodium chloride aqueous solution, dried over anhydrous magnesium sulfate, and concentrated. Purification of the residue by column chromatography on silica gel (using 3:1 mixture of chloroform and ethyl acetate as eluent) gave 3-[2-(4-acetoxybutyl)-3-oxo-2,3-dihydropyridazin-6-yl]-2-phenylpyrazolo[1,5-a]pyridine (2.6 g). An analytical sample was prepared by recrystallization from diisopropyl ether.

mp: 102°-103° C.

IR (Nujol): 1720, 1660 cm$^{-1}$

NMR (CDCl$_3$, δ): 1.7-1.9 (2H, m), 1.9-2.2 (2H, m), 2.05 (3H, s), 4.16 (2H, t-like, J=ca. 6Hz), 4.31 (2H, t-like, J=ca. 6Hz), 6.77 (1H, d, J=10Hz), 6.8-7.0 (1H, m), 7.02 (1H, d, J=10Hz), 7.2-7.4 (1H, m), 7.4-7.5 (3H, m), 7.6-7.7 (2H, m), 7.9-8.0 (1H, m), 8.5-8.6 (1H, m)

MASS m/z: 402, 343, 287

Anal. Calcd. for C$_{23}$H$_{22}$N$_4$O$_3$: C 68.64, H 5.51, N 13.92 (%) Found: C 68.31, H 5.48, N 13.76 (%)

Preparation 7

To an ice-cooled solution of 3-[2-(4-acetoxybutyl)-3-oxo-2,3-dihydropyridazin-6-yl]-2-phenylpyrazolo[1,5-a]pyridine (2.6 g) in methanol (18 ml) was added a solution of sodium hydroxide (0.78 g) in methanol (8 ml). After addition was finished, the mixture was stirred for 15 minutes at room temperature. The reaction mixture was concentrated, and the residue was diluted with chloroform and water. The organic layer was separated and the aqueous layer was extracted twice with chloroform. The combined organic layers were washed with sodium chloride aqueous solution, dried over anhydrous magnesium sulfate, and concentrated.

Purification of the residue by column chromatography on silica gel (using a mixture of chloroform and methanol (25:1) as an eluent) gave 3-[2-(4-hydroxybutyl)-3-oxo-2,3-dihydropyridazin-6-yl]-2-phenylpyrazolo[1,5-a]pyridine (1.8 g). An analytical sample was prepared by recrystallization from toluene.

mp: 115°-116° C.

IR (Nujol): 3400, 1660, 1630 cm$^{-1}$

NMR (CDCl$_3$, δ): 1.6-1.8 (2H, m), 1.9-2.1 (2H, m), 2.41 (1H, broad s), 3.74 (2H, broad t), 4.32 (2H, t-like, J=ca. 7Hz), 6.76 (1H, d, J=9Hz), 6.7-7.0 (1H, m), 7.01 (1H, d, J=9Hz), 7.2-7.4 (1H, m), 7.4-7.5 (3H, m), 7.5-7.7 (2H, m), 7.9-8.0 (1H, m), 8.5-8.6 (1H, m)

MASS m/z: 289, 287 (M$^+$ - 73)

Anal. Calcd. for C$_{21}$H$_{20}$N$_4$O$_2$: C 69.98, H 5.59, N 15.55 (%) Found: C 70.25, H 5.56, N 15.43 (%)

Preparation 8

To a suspension of 3-(3-oxo-2,3-dihydropyridazin-6-yl)-2-phenylpyrazolo[1,5-a]pyridine (1.0 g) and sodium hydride (60% 0.15 g) in N,N-dimethylformamide (10 ml) was added acetoxyethyl bromide (0.58 g) at 5° C., and the resulting mixture was stirred at room temperature for 18 hours. The reaction mixture was poured into ice-water, and extracted twice with ethyl acetate. The extracts were combined, washed successively with 1N sodium hydroxide solution and sodium chloride aqueous solution, dried over magnesium sulfate, and then evaporated in vacuo. The residue was dissolved in 1,4- dioxane (12 ml) and a solution of sodium hydroxide (0.34 g) in water (1.5 ml) was added thereto. The reaction mixture was stirred at 60° C. for 3 hours, and evaporated in vacuo. The residue was treated with water and extracted with chloroform. The extract was washed with sodium chloride aqueous solution, dried over magnesium sulfate, and then evaporated in vacuo. The residue was crystallized from ethyl acetate to afford 3-[2-(2-hydroxyethyl)-3-oxo-2,3-dihydropyridazin-6-yl]-2-phenylpyrazolo[1,5-a]pyridine (0.84 g).

mp: 185.5°–187° C.

IR (Nujol): 3350, 1650, 1580, 1520, 1500 cm$^{-1}$

NMR (CDCl$_3$, $\delta$): 4.05 (2H, m), 4.30 (2H, d, J=4Hz), 6.70 (1H, d, J=10Hz), 6.82 (1H, td, J=7HZ and 1Hz), 7.00 (1H, d, J=10Hz), 7.15–7.60 (6H, m), 7.87 (1H, d, J=10Hz), 8.45 (1H, d, J=7Hz)

MASS: 332 (M+)

Analysis Calcd. for C$_{19}$H$_{16}$N$_4$O$_2$: C 68.66, H 4.85, N 16.86 (%) Found: C 67.29, H 5.05, N 16.42 (%)

EXAMPLE 1

To a suspension of 3-(3-oxo-2,3-dihydropyridazin-6-yl)-2-phenylpyrazolo[1,5-a]pyridine (1.00 g) and sodium hydride (0.37 g, 60%) in N,N-dimethylformamide (5 ml) was added 4-(2-chloroethyl)morpholine hydrochloride (0.98 g). After being stirred for 1.5 hours at 70° C., the reaction mixture was poured into water (100 ml), and extracted twice with methylene chloride.

The combined extracts were washed with water, dried over anhydrous sodium sulfate and evaporated in vacuo. The residue was treated with a 20% solution of hydrogen chloride in ethanol (2 ml) to afford 3-[2-(2-morpholinoethyl)-3-oxo-2,3-dihydropyridazin-6-yl]-2-phenylpyrazolo[1,5-a]pyridine hydrochloride (0.72 g).

mp: 231.5°–233° C.

IR (Nujol): 2325, 1670, 1590 cm$^{-1}$

NMR (CDCl$_3$, $\delta$): 3.18 (2H, m), 3.56 (4H, m), 3.75–4.0 (4H, m), 4.57 (2H, m), 6.93 (1H, d, J=10Hz), 7.13 (1H, t, J=6Hz), 7.14 (1H, d, J=10Hz), 7.40–7.68 (6H, m), 8.05 (1H, d, J=8Hz), 8.93 (1H, d, J=7Hz), 11.04 (1H, broad s)

MASS: 401 (M+)

The following compounds (Examples 2 to 12) were obtained according to a similar manner to that of Example 1.

EXAMPLE 2

3-[2-(2-Piperidinoethyl)-3-oxo-2,3-dihydropyridazin-6-yl]-2-phenylpyrazolo[1,5-a]pyridine hydrochloride mp: 262.5°–265° C.

IR (Nujol): 2495, 1660, 1595 cm$^{-1}$

NMR (DMSO-d$_6$, $\delta$): 1.78 (6H, m), 2.99 (2H, m), 3.45 (4H, m), 4.56 (2H, m), 6.95 (1H, d, J=9Hz), 7.07 (1H, t, J=17Hz), 7.15 (1H, d, J=9Hz), 7.40–7.65 (6H, m), 8.04 (1H, d, J=9Hz), 8.84 (1H, d, J=7Hz), 9.80 (1H, broad s)

MASS: 399 (M+)

EXAMPLE 3

3-[2-(2-Dimethylaminoethyl)-3-oxo-2,3-dihydropyridazin-6-yl]-2-phenylpyrazolo[1,5-a]pyridine hydrochloride mp: 148.5°–149.5° C.

IR (Nujol): 3520, 3450, 2600, 2370, 1640, 1570 cm$^{-1}$

NMR (CDCl$_3$, $\delta$): 2.92 (6H, s), 3.53 (2H, m), 4.77 (2H, m), 6.76 (1H, d, J=10Hz), 6.95 (1H, t, J=6Hz), 7.09 (1H, d, J=10Hz), 7.37–7.64 (6H, m), 8.15 (1H, d, J=8Hz), 8.53 (1H, d, J=7Hz), 13.10 (1H, broad s)

EXAMPLE 4

3-[2-(3-Dimethylaminopropyl)-3-oxo-2,3-dihydropyridazin-6-yl]-2-phenylpyrazolo[1,5-a]pyridine hydrochloride mp: 248°–249° C.

IR (Nujol): 2400 1655 1590 cm$^{-1}$

NMR (DMSO-d$_6$, $\delta$): 2.15 (2H, m), 2.18 (2H, m), 2.75 (6H, s), 4.22 (2H, t, J=7Hz), 7.10 (1H, d, J=10Hz), 7.12 (1H, t, J=7Hz), 7.13 (1H, d, J=10Hz), 7.42–7.63 (6H, m), 7.99 (1H, d, J=12Hz), 8.83 (1H, d, J=8Hz), 10.1 (1H, broad s)

EXAMPLE 5

3-[2-(2-Phthalimidoethyl)-3-oxo-2,3-dihydropyridazin-6-yl]-2-phenylpyrazolo[1,5-a]pyridine mp: 180°–181° C. (recrystallized from ethanol)

IR (Nujol): 1760, 1710, 1660, 1630 cm$^{-1}$

NMR (CDCl$_3$, $\delta$): 4.1–4.3 (2H, m), 4.5–4.6 (2H, m), 6.70 (1H, d, J=10Hz), 6.8–6.9 (1H, m), 6.91 (1H, d, J=10Hz), 7.0–7.1 (1H, m), 7.3–7.7 (10H, m), 8.3–8.4 (1H, m)

MASS m/z: 461, 301, 287

Anal. Calcd. for C$_{27}$H$_{19}$N$_5$O$_3$: C 70.27, H 4.15, N 15.18 (%) Found: C 70.35, H 4.20, N 15.18 (%)

EXAMPLE 6

3-[2-(2-Cyanoethyl)-3-oxo-2,3-dihydropyridazin-6-yl]-2-phenylpyrazolo[1,5-a]pyridine mp: 170°–170.5° C.

IR (Nujol): 1660, 1580 cm$^{-1}$

NMR (CDCl$_3$, $\delta$): 3.00 (2H, t, J=7Hz), 4.55 (2H, t, J=7Hz), 6.77 (1H, d, J=10Hz), 6.94 (1H, t, J=6Hz), 7.06 (1H, d, J=10Hz), 7.26–7.63 (6H, m), 8.14 (1H, d, J=9Hz), 8.53 (1H, d, J=6Hz)

Anal. Calcd.: C 70.36, H 4.43, N 20.52 (%) Found: C 70.49, H 4.41, N 20.62 (%)

EXAMPLE 7

3-[2-(3-Cyanopropyl)-3-oxo-2,3-dihydropyridazin-6-yl]-2-phenylpyrazolo[1,5-a]pyridine mp: 100°–102° C.

IR (Nujol): 1655, 1580 cm$^{-1}$

NMR (CDCl$_3$, $\delta$): 2.2–2.4 (2H, m), 2.51 (2H, t, J=6.9Hz), 4.40 (2H, t, J=6.6Hz), 6.77 (1H, d, J=9.7Hz), 6.94 (1H, td, J=6.9Hz and J=1.3Hz), 7.06 (1H, d, J=9.7Hz), 7.3–7.7 (6H, m), 8.01 (1H, d, J=9.0Hz), 8.54 (1H, d, J=7.0Hz)

MASS: 355

EXAMPLE 8

3-[2-(4-Cyanobutyl)-3-oxo-2,3-dihydropyridazin-6-yl]-2-phenylpyrazolo[1,5-a]pyridine mp: 140°–142° C.

IR (Nujol): 1655, 1590 cm$^{-1}$

NMR (DMSO-d$_6$, $\delta$): 1.5–1.75 (2H, m), 1.8–2.0 (2H, m), 2.5 (2H, t, J=7.0Hz), 4.18 (2H, t, J=6.8Hz), 6.88 (1H, d, J=9.6Hz), 7.0–7.15 (2H, m), 7.35–7.65 (6H, m), 7.95 (1H, d, J=8.9Hz), 8.82 (1H, d, J=6.9Hz)

EXAMPLE 9

3-(2-Benzyl-3-oxo-2,3-dihydropyridazin-6-yl)-2-phenylpyrazolo[1,5-a]pyridine mp: 182.5°–183.5° C.

IR (Nujol): 1670, 1640, 1600, 1530 cm$^{-1}$

NMR (CDCl$_3$, $\delta$): 5.45 (2H, s), 6.76–7.63 (15H, m), 8.50 (1H, d, J=8Hz)

MASS: 378 (M+)

Anal. Calcd.: C 76.17, H 4.79, N 14.80 (%) Found: C 76.44, H 4.84, N 14.78 (%)

EXAMPLE 10

3-[2-(2-Oxo-1,3-oxazolidin-5-yl)methyl-3-oxo-2,3-dihydropyridazin-6-yl]-2-phenylpyrazolo[1,5-a]pyridine mp: 165.5°–166° C.

IR (Nujol): 3350–3400, 1715, 1690, 1645, 1580, 1520, 1495 cm$^{-1}$

NMR (CDCl$_3$, δ): 3.28 (1H, q, J=6Hz), 3.49 (1H, m), 4.24 (1H, m), 4.44 (2H, d, J=5Hz), 5.45 (1H, broad s), 6.80 (1H, d, J=10Hz), 6.91 (1H, t, J=6Hz), 6.95 (1H, d, J=10Hz), 7.26–7.62 (6H, m), 8.00 (1H, d, J=10Hz), 8.54 (1H, d, J=7Hz)

MASS: 387 (M+)

Anal. Calcd. for C$_{21}$H$_{17}$N$_5$O$_3$: C 62.22, H 4.69, N 17.28 (%) Found: C 62.94, H 4.91, N 16.65 (%)

EXAMPLE 11

3-[2-(4-Pyridylmethyl)-3-oxo-2,3-dihydropyridazin-6-yl]-2-phenylpyrazolo[1,5-a]pyridine mp: 165.5°–166° C.

IR (Nujol): 1670, 1630, 1590, 1560, 1530 cm$^{-1}$

NMR (CDCl$_3$, δ): 5.44 (2H, s), 6.80 (1H, d, J=10Hz), 6.90 (1H, t, J=6Hz), 7.05 (1H, d, J=10Hz), 7.19–7.68 (9H, m), 8.51 (1H, d, J=8Hz), 8.64 (2H, s)

MASS: 379 (M+)

Anal. Calcd.: C 72.81, H 4.52, N 18.46 (%) Found: C 73.19, H 4.57, N 18.54 (%)

EXAMPLE 12

3- ( 2-Tetrahydro-2H-pyran-2-yl) -3-oxo-2,3-dihydropyridazin-6-yl ) -2-phenylpyrazolo[1,5 -a]pyridine mp: 165°–165.5° C.

IR (Nujol): 1660, 1630, 1590, 1530 cm$^{-1}$

NMR (CDCl$_3$, δ): 1.52–1.88 (6H, m), 3.44 (1H, t, J=11Hz ) , 4.01 ( 2H, t, J=11Hz ) , 4.31 ( 2H, d, J=6Hz) , 6.77 (1H, d, J=10Hz) , 6.90 (1H, t, J=6Hz) , 6.95 ( 1H, d, J=10Hz ) , 7.26–7.66 ( 6H, m), 8.11 (1H, d, J=10Hz) , 8.52 (1H, d, J=6Hz)

MASS: 386 (M+)

Anal. Calcd. for C$_{23}$H$_{22}$N$_3$O$_2$: C 71.48, H 5.47, N 14.50 (%) Found: C 71.26, H 5.67, N 14.45 (%)

EXAMPLE 13

A mixture of 3-[2-(2-phthalimidoethyl)-3-oxo-2,3-dihydropyridazin-6-yl]-2-phenylpyrazolo[1,5-a]pyridine (2.2 g), hydrazine monohydrate (2 ml), and ethanol (100 ml) was stirred for 1 hour under reflux. After being cooled to room temperature, the reaction mixture was concentrated, and the residue was partitioned between chloroform and water. The organic layer was separated, and extracted with 10% hydrochloric acid. The aqueous layer was washed twice with chloroform, neutralized with sodium hydroxide, and extracted three times with chloroform. The combined organic layers were washed with water and sodium chloride aqueous solution, dried over anhydrous magnesium sulfate, and concentrated to give 3-[2-(2-aminoethyl)-3-oxo-2,3-dihydropyridazin-6-yl]-2-phenylpyrazolo[1,5-a]pyridine (1.5 g). An analytical sample was prepared by recrystallization from ethyl acetate.

mp: >142° C.

IR (Nujol): 3380, 3300, 1660, 1630 cm$^{-1}$

NMR (CDCl$_3$, δ): 1.47 (2H, broad s), 3.25 (2H, t-like, J=ca. 6Hz), 4.35 (2H, t-like, J=ca. 6Hz), 6.78 (1H, d, J=10Hz), 6.9–7.0 (1H, m), 7.04 (1H, d, J=10Hz), 7.3–7.4 (1H, m), 7.4–7.5 (3H, m), 7.6–7.7 (2H, m), 7.9–8.0 (1H, m), 8.5–8.6 (1H, m)

MASS m/z: 331, 302

EXAMPLE 14

To an ice-cooled solution of 3-[2-(2-aminoethyl)-3-oxo-2,3-dihydropyridazin-6-yl]-2-phenylpyrazolo[1,5-a]-pyridine (1.5 g), triethylamine (1.5 ml), and N,N-dimethylformamide (15 ml) was added ethyl 2-bromoacetate (0.60 ml), and the mixture was stirred for 1 hour at room temperature. The reaction mixture was concentrated, and the residue was partitioned between chloroform and water. The organic layer was separated, washed with sodium chloride aqueous solution, dried over anhydrous magnesium sulfate, and concentrated. Purification of the residue by column chromatography on silica gel (gradient elution, using 50:1 and 25:1 mixture of chloroform and methanol) gave 3-[2-{2-(ethoxycarbonylmethylamino)ethyl}-3-oxo-2,3-dihydropyridazin-6-yl]-2-phenylpyrazolo[1,5-a]pyridine (0.90 g).

mp: 212°–214° C.

IR (Nujol): 2750, 2170, 2120, 2430, 1760, 1650, 1630 cm$^{-1}$

NMR (CDCl$_3$, δ): 1.24 (3H, t, J=7Hz), 3.72 (2H, broad t, J=ca. 5Hz), 4.04 (2H, s), 4.21 (2H, q, J=7Hz), 4.79 (2H, broad t, J=ca. 5Hz), 6.79 (1H, d, J=10Hz), 6.8–6.9 (1H, m), 7.05 (1H, d, J=10Hz), 7.3–7.5 (4H, m), 7.6–7.7 (2H, m), 8.0–8.1 (1H, m), 8.4–8.5 (1H, m), 9.2–11.0 (1H, broad m)

MASS m/z: 417, 344, 315, 302

EXAMPLE 15

To a solution of 3-[2-{2-(ethoxycarbonylmethylamino)ethyl}-3-oxo-2,3-dihydropyridazin-6-yl]-2-phenylpyrazolo[1,5-a]pyridine (0.80 g) in ethanol (8 ml) was added a solution of sodium hydroxide (0.15 g) in water (4 ml) and the mixture was stirred for 0.5 hour at room temperature. The reaction mixture was concentrated and the residue was partitioned between water and ethyl acetate. The aqueous layer was separated, neutralized with 1N hydrochloric acid to give the precipitate, which was collected and purified by recrystallization from 50% aqueous ethanol to give 3-[2-{2-(carboxymethylamino)ethyl}-3-oxo-2,3-dihydropyridazin-6-yl]-2-phenylpyrazolo[1,5-a]pyridine (0.50 g).

mp: 230°–232° C.

IR (Nujol): 3400, 1650, 1600 cm$^{-1}$

NMR (CDCl$_3$-CD$_3$OD=1:1, δ): 3.19 (2H, broad t, J=ca. 6Hz), 3.22 (2H, s), 4.30 (2H, broad t, J=ca. 6Hz), 6.54 (1H, d, J=10Hz), 6.7–6.8 (1H, m), 6.83 (1H, d, J=10Hz), 7.1–7.2 (4H, m), 7.2–7.4 (2H, m), 7.7–7.8 (1H, m), 8.2–8.3 (1H, m)

EXAMPLE 16

A mixture of 3-[2-(2-aminoethyl)-3-oxo-2,3-dihydropyridazin-6-yl]-2-phenylpyrazolo[1,5-a]pyridine (0.50 g), 1-[(2,3-epoxypropyl)oxy]naphthalene (0.36 g), and 1,4-dioxane (15 ml)-water (1.5 ml) was stirred for 1 hour at 50° C., and then for 2 hours under reflux.

After being cooled to room temperature, the reaction mixture was concentrated, and the residue was purified by column chromatography on silica gel (gradient elution, using 50:1 and 25:1 mixture of chloroform and methanol) to give 3-[2-{2-{2-hydroxy-3-(1-naphthyloxy)propylamino}-ethyl}-3-oxo-2,3-dihydropyridazin-6-yl]-2-phenylpyrazolo[1,5-a]pyridine (0.49 g).

NMR (CDCl$_3$, δ): 2.0–3.0 (2H, broad m), 2.9–3.1 (2H, m), 3.1–3.4 (2H, m), 4.0–4.3 (3H, m), 4.3–4.6 (2H, m), 6.7–6.8 (2H, m), 6.8–6.9 (1H, m), 6.98 (1H, d, J=10Hz), 7.0–7.5 (8H, m), 7.5–7.6 (2H, m), 7.7–7.8 (1H, m), 7.9–8.0 (1H, m), 8.1–8.2 (1H, m), 8.4–8.5 (1H, m)

MASS m/z: 532 (M$^+$ +1)

EXAMPLE 17

3-[2-}2-}2-Hydroxy-3-(1-naphthyloxy)-propylamino}-ethyl}-3-oxo-2,3-dihydropyridazin-6-yl]-2-phenylpyrazolo[1,5-a]pyridine hydrochloride was obtained according to a conventional manner from the compound obtained in Example 16.

IR (Nujol): 3300 (br), 1650, 1630 cm$^{-1}$

NMR (DMSO-d$_6$, δ): 3.2–3.6 (4H, m), 4.1–4.2 (2H, m), 4.3–4.7 (1H, broad m), 4.59 (2H, broad m), 6.10 (1H, broad m), 6.94 (1H, d, J=10Hz), 6.9–7.0 (1H, m), 7.0–7.2 (1H, m), 7.13 (1H, d, J=10Hz), 7.3–7.6 (8H, m), 7.6–7.7 (2H, m), 7.8–7.9 (1H, m), 8.0–8.1 (1H, m), 8.2–8.3 (1H, m), 8.8–9.0 (1H, m), 9.0–9–3 (1H, broad m), 9.3–9.7 (1H, broad m)

EXAMPLE 18

To an ice-cooled solution of 3-[2-(4-hydroxybutyl)-3-oxo-2,3-dihydropyridazin-6-yl]-2-phenylpyrazolo[1,5-a]pyridine (1.5 g) in methylene chloride (15 ml) was added thionyl chloride (0.37 ml), and the solution was stirred for 0.5 hour at room temperature. Additional thionyl chloride (0.37 ml) was added to the mixture, and stirring was continued for 1 hour at room temperature followed by 1 hour at 40° C. Again, additional thionyl chloride (0.37 ml) was added, and the mixture was stirred for 1 hour under reflux. After being cooled to room temperature, the reaction mixture was concentrated to give the intermediate chloride compound.

To a solution of this intermediate chloride compound in sec-butyl alcohol (15 ml) was added 50% aqueous solution of dimethylamine (10 ml), and the mixture was stirred for 6 hours under reflux. After being cooled to room temperature, the reaction mixture was concentrated. The residue was dissolved in 1N hydrochloric acid and washed with ethyl acetate. The aqueous layer was separated, neutralized with sodium hydroxide, and extracted three times with chloroform. The combined organic layers were washed with saturated aqueous solution of sodium bicarbonate and sodium chloride aqueous solution, dried over anhydrous magnesium sulfate, and concentrated. Purification of the residue by column chromatography on silica gel (gradient elution, using 10:1 and 5:1 mixture of chloroform and methanol) gave 3-[2-(4-dimethylaminobutyl)-3-oxo-2,3-dihydropyridazin-6-yl]-2-phenylpyrazolo[1,5-a]pyridine.

This amine was dissolved in ethanol (5 ml) and treated with 20% solution of hydrogen chloride in ethanol (5 ml). The mixture was concentrated, and the residue was purified by recrystallization from a mixture of ethanol and diisopropyl ether to give 3-[2-(4-dimethylaminobutyl)-3-oxo-2,3-dihydropyridazin-6-yl]-2-phenylpyrazolo[1,5-a]pyridine hydrochloride (0.89 g).

mp: 215° to 216° C.

IR (Nujol): 3100, 3050, 2400, 1660, 1630 cm$^{-1}$

NMR (DMSO-d$_6$, δ): 1.6–2.0 (4H, broad m), 2.70 (6H, s), 3.08 (2H, broad s), 3.40 (1H, broad s), 4.1–4.2 (2H, broad m), 6.89 (1H, d, J=10Hz), 7.0–7.1 (1H, m), 7.10 (1H, d, J=10Hz), 7.4–7.5 (4H, m), 7.5–7.7 (2H, m), 7.97 (1H, m), 8.83 (1H, m)

MASS m/z: 387, 329

EXAMPLE 19

A solution of 3-[2-(2-hydroxyethyl)-3-oxo-2,3-dihydropyridazin-6-yl]-2-phenylpyrazolo[1,5-a]pyridine (0.5 g) and thionyl chloride (0.13 ml) in methylene chloride (4 ml) was stirred at room temperature for 1 hour and evaporated in vacuo. To the residue was added dropwise a solution of 1-(2-hydroxyethyl)piperazine (0.78 g) in amyl alcohol (5 ml), and the suspension was refluxed for 1.5 hours. The reaction mixture was evaporated in vacuo, and the residue was purified by column chromatography on silica gel using chloroform as eluent. The obtained oil was treated with a 20% solution of hydrogen chloride in ethanol to afford 3-[2-}2-}4-(2-hydroxyethyl)piperazin- 1-yl}ethyl}-3-oxo-2,3-dihydropyridazin-6-yl]-2-phenylpyrazolo[1,5-a]pyridine dihydrochloride.

mp: 240°–241.5° C.

IR (Nujol): 3400, 1660, 1590 cm$^{-1}$

NMR (DMSO-d$_6$, δ): 3.42–3.79 (17H, m), 4.51 (2H, broad s), 6.90 (1H, d, J=10Hz), 7.08 (1H, t, J=6Hz), 7.10 (1H, d, J=10Hz), 7.40–7.70 (6H, m), 8.06 (1H, d, J=9Hz), 8.83 (1H, d, J=6Hz)

Anal. Calcd.: C 55.25, H 6.08, N 15.47 (%) Found: C 55.16, H 6.32, N 15.18 (%)

EXAMPLE 20

3-[2-{2-{4-(2-Methoxyphenyl)piperazin-1-yl}ethyl}-3-oxo-2,3-dihydropyridazin-6-yl]-2-phenylpyrazolo[1,5-a]pyridine was obtained according to a similar manner to that of Example 19.

mp: 120°–125° C.

IR (Nujol): 1680, 1585, 1525, 1500 cm$^{-1}$

NMR (CDCl$_3$, δ): 2.84 (4H, m), 2.97 (2H, t, J=6Hz), 3.13 (4H, m), 3.87 (3H, s), 4.47 (2H, t, J=6Hz), 6.76 (1H, d, J=10Hz), 6.85–7.65 (12H, m), 8.05 (1H, d, J=10Hz), 8.53 (1H, d, J=7Hz)

MASS: 506 (M$^+$ - 1)

Anal. Calcd.: C 71.13, H 5.97, N 16.59 (%) Found: C 71.17, H 5.96, N 16.58 (%)

EXAMPLE 21

A mixture of 3-[2-(2-cyanoethyl)-3-oxo-2,3-dihydropyridazin-6-yl]-2-phenylpyrazolo[1,5-a]pyridine (0.35 g), sodium azide (0.20 g) and triethylamine hydrochloride (0.21 g) in N-methylpyrrolidone (10 ml) was stirred at 150° C. for 4 hours under nitrogen atmosphere. The reaction mixture was poured into water (30 ml), acidified with 10% hydrochloric acid (5 ml), and extracted twice with ethyl acetate. The combined extracts were washed with water, dried over magnesium sulfate and evaporated in vacuo. The residue was purified by column chromatography on silica gel using a mixture of chloroform and methanol (20:1) as an eluent. The fractions containing the object compound were combined and evaporated in vacuo. The residue was recrystallized from ethyl acetate to give 3-[2-{2-(1H-tetrazol-5-yl)ethyl}-3-oxo-2,3-dihydropyridazin-6-yl]-2-phenylpyrazolo[1,5-a]pyridine (0.06 g).

mp: 230°–232° C. (decomp.)

IR (Nujol): 1660, 1585 cm$^{-1}$

NMR (CDCl$_3$, δ): 3.74 (2H, t, J=6Hz), 4.83 (2H, t, J=6Hz), 6.90 (1H, d, J=10Hz), 6.98 (1H, t, J=6Hz), 7.15 (1H, d, J=10Hz), 7.26–7.58 (6H, m), 7.96 (1H, d, J=7Hz), 8.56 (1H, d, J=6Hz), 11.96 (1H, broad s)

The following compounds (Examples 22 and 23) were obtained according to a similar manner to that of Example 21.

EXAMPLE 22

3-[2-{3-(1H-Tetrazol-5-yl)propyl}-3-oxo-2,3-dihydropyridazin-6-yl]-2-Phenylpyrazolo[1,5-a]pyridine
mp: 215°–217° C.
IR (Nujol): 1665, 1595 cm$^{-1}$
NMR (DMSO-d$_6$, δ): 2.15–2.35 (2H, m), 3.00 (2H, t, J=7.6Hz), 4.26 (2H, t, J=6.9Hz), 6.86 (1H, d, J=9.7Hz), 7.05–7.15 (2H, m), 7.35–7.65 (6H, m), 7.96 (1H, d, J=8.9Hz), 8.82 (1H, d, J=6.9Hz)
MASS: 398, 355, 287
Anal. Calcd. for C$_{21}$H$_{18}$N$_8$O: C 63.31, N 4.55, H 28.12 (%) Found: C 63.03, N 4.53, H 27.98 (%)

EXAMPLE 23

3-[2-{4-(1H-Tetrazol-5-yl)butyl}-3-oxo-2,3-dihydropyridazin-6-yl]-2-phenylpyrazolo[1,5-a]pyridine
mp: 213° to 214° C.
IR (Nujol): 1635, 1565 cm$^{-1}$
NMR (DMSO-d$_6$, δ): 1.7–2.0 (4H, m), 2.97 (2H, t, J=6.7Hz), 4.19 (2H, m), 6.88 (1H, d, J=9.7Hz), 7.0–7.2 (2H, m), 7.35–7.5 (4H, m), 7.5–7.65 (2H, m), 7.89 (1H, d, J=8.9Hz), 8.82 (1H, d, J=6.9Hz)

EXAMPLE 24

A solution of 3-[2-(2-hydroxyethyl)-3-oxo-2,3-dihydropyridazin-6-yl]-2-phenylpyrazolo[1,5-a]pyridine (0.5 g) and thionyl chloride (0.13 ml) in methylene chloride (4 ml) was stirred at room temperature for 1 hour and then evaporated in vacuo. To the residue were added, Triton B (2.04 g) and methylene chloride (4 ml). The reaction mixture was refluxed for 2 hours, poured into water (10 ml) and extracted with chloroform. The extract was washed with water, dried over magnesium sulfate and evaporated in vacuo.

The residue was purified by column chromatography on silica gel using chloroform as an eluent. The obtained oil was crystallized from a mixture of ethanol and ethyl acetate (1:1) to afford 3-(2-vinyl-3-oxo-2,3-dihydropyridazin-6-yl)-2-phenylpyrazolo[1,5-a]pyridine.
mp: 187.5°–188° C.
IR (Nujol): 1680, 1635, 1605 cm$^{-1}$
NMR (CDCl$_3$, δ): 5.05 (1H, d, J=10Hz), 5.87 (1H, d, J=16Hz), 6.77 (1H, d, J=10Hz), 6.94–7.03 (2H, m), 7.26–7.66 (6H, m), 7.87 (1H, dd, J=16Hz and 10Hz), 8.10 (1H, d, J=10Hz), 8.55 (1H, d, J=7Hz)
Anal. Calcd.: C 72.60, H 4.49, N 17.83 (%) Found: C 72.85, H 4–62, N 18.00 (%)

EXAMPLE 25

A mixture of 3-(3-oxo-2,3-dihydropyridazin-6-yl)-2-phenylpyrazolo[1,5-a]pyridine (0.60 g), 2,2-dimethyl-3,4-epoxy-6-cyano-3,4-dihydro-2H-chromene (0.80 g), and 60% sodium hydride (0.16 g) in dimethylsulfoxide (6 ml) was stirred for 5 hours at 60° C., and then diluted with ethyl acetate. The mixture was washed with water (10 ml) and sodium chlroide aqueous solution (10 ml), dried over magnesium sulfate, and evaporated in vacuo. The residue was chromatographed on silica gel (10 g) with a mixture of n-hexane and ethyl acetate (2:1). The fractions containing the object compound were combined and evaporated in vacuo. The residue was recrystallized from a mixture of ethyl acetate and diisopropyl ether to give 3-[2-(2,2-dimethyl-3-hydroxy-6-cyano-3,4-dihydro-2H-chromen-4-yl)-3-oxo-2,3-dihydropyridazin-6-yl]-2-phenylpyrazolo[1,5-a]pyridine (0.51 g).
mp: 209°–210° C.
IR (Nujol): 3330, 2220, 1670, 1600 cm$^{-1}$
NMR (CDCl$_3$, δ): 1.41 (3H, s), 1.56 (3H, s), 3.32 (1H, d, J=5.8Hz), 4.25 (1H, m), 6.35 (1H, d, J=9.0Hz), 6.3–7.2 (7H, m), 7.4–7.6 (6H, m), 8.45 (1H, d, J=6.9Hz)
MASS: 489 (M+), 456, 287
Anal. Calcd.: C 71.15, H 4.74, N 14.31 (%) Found: C 70.97, H 4.75, N 14.06 (%)

Preparation 9

Potassium iodide (0.1 g) and 1,5-dibromopentane (4.6 g) were added to a suspension of 3-(3-oxo-2,3-dihydropyridazin-6-yl)-2-phenylpyrazolo[1,5-a]pyridine (2.88 g) and 60% sodium hydride (0.4 g) in N,N-dimethylformamide (40 ml). After being stirred for 3 hours at room temperature, the mixture was poured into cold water and extracted with ethyl acetate. The extract was washed with water, dried over magnesium sulfate, and evaporated in vacuo. The oily residue was purified by column chromatography on silica gel (100 g) using chloroform as an eluent to afford 3-[2-(5-bromopentyl)-3-oxo-2,3-dihydropyridazin-6-yl]-2-phenyl-pyrazolo[1,5-a]pyridine (3.48 g).
mp: 111° to 112° C. (recrystallized from a mixture of diethyl ether and ethyl acetate)
IR (Nujol): 1660, 1650 (shoulder), 1625, 1580 cm$^{-1}$
NMR (CDCl$_3$, δ): Ca. 1.5–2.1 (6H, m), 3.44 (2H, t, J=6.7Hz), 4.29 (2H, t, J=7.2Hz), 6.77 (1H, d, J=9.6Hz), 6.92 (1H, t, J=6.9Hz), 7.02 (1H, d, J=9.6Hz), 7.33 (1H, t, J=6.8Hz), 7.42–7.64 (5H, m), 7.98 (1H, d, J=7.9Hz), 8.53 (1H, d, J=6.9Hz)

The following compounds (Preparations 10 to 15) were obtained according to a similar manner to that of Preparation 9.

Preparation 10

3-[2-(6-Bromohexyl)-3-oxo-2,3-dihydropyridazin-6-yl]-2-phenylpyrazolo[1,5-a]pyridine
mp: 94° to 95° C.
IR (Nujol): 1655, 1630, 1590 cm$^{-1}$
NMR (CDCl$_3$, δ): Ca. 1.3–1.7 (4H, m), Ca. 1.7–2.1 (4H, m), 3.42 (2H, t, J=6.7Hz), 4.27 (2H, t, J=7.3Hz), 6.77 (1H, d, J=9.6Hz), 6.93 (1H, t, J=6.9Hz), 7.02 (1H, d, J=9.6Hz), 7.29–7.37 (1H, m), 7.44–7.47 (3H, m), 7.59–7.64 (2H, m), 7.97 (1H, d, J=8.9Hz), 8.55 (1H, d, J=6.9Hz)

Preparation 11

3-[2-(7-Bromoheptyl)-3-oxo-2,3-dihydropyridazin-6-yl]-2-phenylpyrazolo[1,5-a]pyridine
IR (Film/NaCl): 1655, 1630, 1585 cm$^{-1}$
NMR (CDCl$_3$, δ): Ca. 1.3–2.2 (10H, m), 3.41 (2H, t, J=6.8Hz), 4.27 (2H, t, J=7.4Hz), 6.76 (1H, d, J=9.6Hz), 6.92 (1H, t, J=6.9Hz), 7.01 (1H, d, J=9.6Hz), 7.32 (1H, t, J=6.8 Hz), 7.42–7.64 (5H, m), 7.98 (1H, d, J=7.9Hz), 8.53 (1H, d, J=6.9Hz)

Preparation 12

3-[2-(8-Bromooctyl)-3-oxo-2,3-dihydropyridazin-6-yl]-2-phenylpyrazolo[1,5-a]pyridine
mp: 84° to 85° C.
IR (Nujol): 1655, 1630, 1580 cm$^{-1}$
NMR (CDCl$_3$, δ): Ca. 1.2–1.7 (8H, broad), Ca. 1.7–2.1 (4H, m), 3.40 (2H, t, J=6.8Hz), 4.27 (2H, t, J=7.4Hz), 6.76 (1H, d, J=9.6Hz), 6.92 (1H, t, J=6.9Hz), 7.01 (1H, d, J=9.6Hz), 7.27–7.35 (1H, m), 7.43–7.47 (3H, m), 7.58–7.64 (2H, m), 7.97 (1H, d, J=8.9Hz), 8.53 (1H, d, J=6.9Hz)

Preparation 13

3-[2-(9-Bromononyl)-3-oxo-2,3-dihydropyridazin-6-yl]-2-phenylpyrazolo[1,5-a]pyridine mp: 85° to 87° C.

IR (Nujol): 1650, 1625, 1580, 1520 cm$^{-1}$

NMR (CDCl$_3$, δ): 1.20–1.67 (10H, m), 1.67–2.20 (4H, m), 3.40 (2H, t, J=6.8Hz), 4.27 (2H, t, J=7.4Hz), 6.77 (1H, d, J=9.6Hz), 6.96 (1H, t, J=6.9Hz), 7.00 (1H, d, J=9.6Hz), 7.32 (1H, m), 7.40–7.50 (3H, m), 7.50–7.68 (2H, m), 7.98 (1H, d, J=8.9Hz), 8.55 (1H, d, J=7.0Hz)

Preparation 14

3-[2-(10-Bromodecyl)-3-oxo-2,3-dihydropyridazin-6-yl]-2-phenylpyrazolo[1,5-a]pyridine mp: 59° to 60° C.

IR (Nujol): 1650, 1625, 1585, 1520 cm$^{-1}$

NMR (CDCl$_3$, δ): 1.20–1.57 (12H, m), 1.70–2.03 (4H, m), 3.40 (2H, t, J=6.8Hz), 4.27 (2H, t, J=7.4Hz), 6.76 (1H, d, J=9.6Hz), 6.92 (1H, t, J=6.9Hz), 7.00 (1H, d, J=9.6Hz), 7.31 (1H, m), 7.37–7.52 (3H, m), 7.53–7.68 (2H, m), 7.98 (1H, d, J=8.9Hz), 8.54 (1H, d, J=7.0Hz)

Preparation 15

3-[2-(12-Bromododecyl)-3-oxo-2,3-dihydropyridazin-6-yl]-2-phenylpyrazolo[1,5-a]pyridine mp: 70° to 71° C.

IR (Nujol): 1655, 1630, 1590, 1525 cm$^{-1}$

NMR (CDCl$_3$, δ): 1.13–1.53 (16H, m), 1.73–2.03 (4H, m), 3.40 (2H, t, J=6.8Hz), 4.27 (2H, t, J=7.4Hz), 6.76 (1H, d, J=9.6Hz), 6.92 (1H, t, J=6.9Hz), 7.00 (1H, d, J=9.6Hz), 7.31 (1H, m), 7.37–7.50 (3H, m), 7.55–7.67 (2H, m), 7.98 (1H, d, J=8.9Hz), 8.53 (1H, d, J=6.0Hz)

EXAMPLE 26

A mixture of 3-[2-(5-bromopentyl)-3-oxo-2,3-dihydropyridazin-6-yl]-2-phenylpyrazolo[1,5-a]pyridine (2.753 g) and sodium cyanide (0.37 g) in dimethyl sulfoxide (12.6 ml) was stirred at room temperature for 2 hours and then at 60° C. for 1 hour. To the mixture was added water and extracted with ethyl acetate. The extract was washed with water, dried over magnesium sulfate, and evaporated in vacuo. The residue was purified by column chromatography on silica gel using a mixture of chloroform and methanol as an eluent to afford 3-[2-(5-cyanopentyl)-3-oxo-2,3-dihydropyridazin-6-yl]-2-phenylpyrazolo[1,5-a]pyridine (1.75 g).

mp: 120.5° to 122° C. (recrystallized from ethyl acetate)

IR (Nujol): 2245 (weak), 1660, 1630 (shoulder), 1590 cm$^{-1}$

NMR (CDCl$_3$, δ): Ca. 1.5–2.1 (6H, m), 2.39 (2H, t, J=6.8Hz), 4.29 (2H, t, J=7.3Hz), 6.77 (1H, d, J=9.6Hz), 6.93 (1H, t, J=6.9Hz), 7.03 (1H, d, J=9.6Hz), 7.34 (1H, t, J=6.8Hz), 7.44–7.64 (5H, m), 7.96 (1H, d, J=7.8Hz), 8.54 (1H, d, J=7Hz)

The following compounds (Examples 27 to 32) were obtained according to a similar manner to that of Example 26.

EXAMPLE 27

3-[2-(6-Cyanohexyl)-3-oxo-2,3-dihydropyridazin-6-yl]-2-phenylpyrazolo[1,5-a]pyridine mp: 85° to 87° C.

IR (Nujol): 2245 (weak), 1660, 1630, 1590 cm$^{-1}$

NMR (CDCl$_3$, δ): Ca. 1.4–1.8 (6H, m), Ca. 1.8–2.1 (2H, m), 2.36 (2H, t, J=6.8Hz), 4.27 (2H, t, J=7.2Hz), 6.77 (1H, d, J=9.6Hz), 6.93 (1H, t, J=6.9Hz), 7.02 (1H, d, J=9.6Hz), 7.29–7.38 (1H, m), 7.44–7.58 (3H, m), 7.59–7.64 (2H, m), 7.97 (1H, d, J=8.9Hz), 8.54 (1H, d, J=6.9Hz)

EXAMPLE 28

3-[2-(7-Cyanoheptyl)-3-oxo-2,3-dihydropyridazin-6-yl]-2-phenylpyrazolo[1,5-a]pyridine mp: 112° to 113° C. (recrystallized from ethyl acetate)

IR (Nujol): 2250 (weak), 1660, 1630, 1590 cm$^{-1}$

NMR (CDCl$_3$, δ): Ca. 1.4–2.1 (10H, m), 2.34 (2H, t, J=6.9Hz), 4.27 (2H, t, J=7.3Hz), 6.76 (1H, d, J=9.6Hz), 6.95 (1H, t, J=6.9Hz), 7.02 (1H, d, J=9.6Hz), 7.33 (1H, t, J=6.8Hz), 7.43–7.64 (5H, m), 7.98 (1H, d, J=8.9Hz), 8.53 (1H, d, J=7Hz)

EXAMPLE 29

3-[2-(8-Cyanooctyl)-3-oxo-2,3-dihydropyridazin-6-yl]-2-phenylpyrazolo[1,5-a]pyridine mp: 94° to 96° C.

IR (Nujol): 2230 (weak), 1650, 1580 cm$^{-1}$

NMR (CDCl$_3$, δ): Ca. 1.2–1.8 (10H, broad), Ca. 1.8–2.1 (2H, m), 1.89–1.92 (2H, m), 2.33 (2H, t, J=6.9Hz), 4.27 (2H, t, J=7.4Hz), 6.76 (1H, d, J=9.6Hz), 6–92 (1H, t, J=6.9Hz), 7.01 (1H, d, J=9.6Hz), 7.27–7.36 (1H, m), 7.44–7.58 (3H, m), 7.58–7.64 (2H, m), 7.98 (1H, d, J=8.9Hz), 8.53 (1H, d, J=6.9Hz)

EXAMPLE 30

3-[2-(9-Cyanononyl)-3-oxo-2,3-dihydropyridazin-6-yl]-2-phenylpyrazolo[1,5-a]pyridine mp: 123° to 125° C.

IR (Nujol): 2240, 1655, 1630, 1585, 1525 cm$^{-1}$

NMR (CDCl$_3$, δ): 1.20–1.53 (10H, m), 1.53–1.73 (2H, m), 1.80–2.03 (2H, m), 2.33 (2H, t, J=7.0Hz), 4.27 (2H, t, J=7.4Hz), 6.76 (1H, d, J=9.6Hz), 6.92 (1H, t, J=7.2Hz), 7.01 (1H, d, J=9.6Hz), 7.32 (1H, m), 7.40–7.55 (3H, m), 7.55–7.77 (2H, m), 7.98 (1H, d, J=8.9Hz), 8.54 (1H, d, J=6.9Hz)

EXAMPLE 31

3-[2-(10-Cyanodecyl)-3-oxo-2,3-dihydropyridazin-6-yl]-2-phenylpyrazolo[1,5-a]pyridine mp: 77° to 79° C.

IR (Nujol): 2240, 1645, 1580, 1520 cm$^{-1}$

NMR (CDCl$_3$, δ): 1.20–1.53 (12H, m), 1.53–1.75 (2H, m), 1.75–2.05 (2H, m), 2.33 (2H, t, J=7.0Hz), 4.27 (2H, t, J=7.4Hz), 6.76 (1H, d, J=9.6Hz), 6.92 (1H, t, J=6.9Hz), 7.00 (1H, d, J=9.6Hz), 7.31 (1H, m), 7.37–7.53 (3H, m), 7.53–7.70 (2H, m), 7.98 (1H, d, J=8.9Hz), 8.53 (1H, d, J=6.9Hz)

EXAMPLE 32

3-[2-(12-Cyanododecyl)-3-oxo-2,3-dihydropyridazin-6-yl]-2-phenylpyrazolo[1,5-a]pyridine mp: 69° to 70° C.

IR (Nujol): 2240, 1655, 1630, 1585, 1530 cm$^{-1}$

NMR (CDCl$_3$, δ): 1.20–1.55 (16H, m), 1.55–1.73 (2H, m), 1.83–2.03 (2H, m), 2.33 (2H, t, J=7.0Hz), 4.27 (2H, t, J=7.4Hz), 6.76 (1H, d, J=9.6Hz), 6.91 (1H, t, J=6.9Hz), 7.00 (1H, d, J=9.6Hz), 7.31 (1H, m), 7.37–7.50 (3H, m), 7.53–7.68 (2H, m), 7.98 (1H, d, J=8.9Hz), 8.53 (1H, d, J=6.9Hz)

EXAMPLE 33

3-[2-Cyanomethyl-3-oxo-2,3-dihydropyridazin-6-yl]-2-phenylpyrazolo[1,5-a]pyridine was obtained according to a similar manner to that of Example 1.

mp: 218°–219° C.

IR (Nujol): 1670, 1660 (shoulder), 1625, 1590 cm$^{-1}$

NMR (CDCl$_3$, δ): 5.18 (2H, s), 6.78 (1H, d, J=9.8Hz), 6.97 (1H, t, J=6.9Hz), 7.05 (1H, d, J=9.8Hz), 7.39 (1H, t, J=8Hz), 7.46–7.63 (5H, m), 8.15 (1H, d, J=9Hz), 8.55 (1H, d, J=6.9Hz)

The following compounds (Examples 34 to 41) were obtained according to a similar manner to that of Example 21.

EXAMPLE 34

3-[2-{(1H-Tetrazol-5-yl)methyl}-3-oxo-2,3-dihydropyridazin-6-yl]-2-phenylpyrazolo[1,5-a]pyridine mp: 252° to 254° C. (decomp.), (recrystallized from a mixture of chloroform and methanol)

IR (Nujol): 1650, 1580 cm$^{-1}$

NMR (DMSO-d$_6$, δ): 5.72 (2H, s), 6.97 (1H, d, J=9.7Hz), 7.07 (1H, t, J=6.8Hz), 7.11 (1H, d, J=9.7Hz), 7.40 (1H, t, J=6.8Hz), 7.47–7.66 (5H, m), 7.83 (1H, d, J=8.9Hz), 8.82 (1H, d, J=6.9Hz)

EXAMPLE 35

3-[2-{5-(1H-Tetrazol-5-yl)pentyl}-3-oxo-2,3-dihydropyridazin-6-yl]-2-phenylpyrazolo[1,5-a]pyridine mp: 167° to 168° C. (recrystallized from a mixture of methanol and ethyl acetate)

IR (Nujol): 1635, 1560 cm$^{-1}$

NMR (DMSO-d$_6$, δ): Ca. 1.3–1.5 (2H, m), Ca. 1.7–1.9 (4H, m), 2.90 (2H, t, J=7.4Hz), 4.14 (2H, t, J=7.1Hz), 6.87 (1H, d, J=9.6Hz), Ca. 7.1 (1H, m), 7.10 (1H, d, J=9.6Hz), Ca. 7.4–7.7 (6H, m), 7.92 (1H, d, J=8.9Hz), 8.83 (1H, d, J=6.9Hz)

EXAMPLE 36

3-[2-{6-(1H-Tetrazol-5-yl)hexyl}-3-oxo-2,3-dihydropyridazin-6-yl]-2-phenylpyrazolo[1,5-a]pyridine mp: 183° to 185° C. (recrystallized from ethanol)

IR (Nujol): 1640, 1560 cm$^{-1}$

NMR (CDCl$_3$, δ): Ca. 1.3–1.7 (4H broad), Ca. 1.7–2.1 (4H, m), 3.03 (2H, t, J=7.1Hz), 4.31 (2H, t, J=7.0Hz), 6.87 (1H, d, J=9.6Hz), 6.95 (1H, t, J=6.9Hz), 7.12 (1H, d, J=9.6Hz), 7.32–7.39 (1H, m), 7.45–7.48 (3H, m), 7.58–7.63 (2H, m), 7.99 (1H, d, J=8.9Hz), 8.55 (1H, d, J=6.9Hz)

EXAMPLE 37

3-[2-{7-(1H-Tetrazol-5-yl)heptyl}-3-oxo-2,3-dihydropyridazin-6-yl]-2-phenylpyrazolo[1,5-a]pyridine mp: 189.5° to 190.5° C. (recrystallized from a mixture of methanol and ethyl acetate)

IR (Nujol): 1650, 1580 cm$^{-1}$

NMR (DMSO-d$_6$, δ): Ca. 1.2–1.9 (10H, m), 2.87 (2H, t, J=7.5Hz), 4.13 (2H, t, J=7.1Hz), 6.87 (1H, d, J=9.6Hz), Ca. 7.1 (1H, m), 7.11 (1H, d, J=9.6Hz), Ca. 7.4–7.7 (6H, m), 7.91 (1H, d, J=8.9Hz), 8.82 (1H, d, J=6.9Hz)

EXAMPLE 38

3-[2-{8-(1H-Tetrazol-5-yl)octyl}-3-oxo-2,3-dihydropyridazin-6-yl]-2-phenylpyrazolo[1,5-a]pyridine mp: 165° to 167° C. (recrystallized from ethanol)

IR (Nujol): 1635, 1550–1565 (broad) cm$^{-1}$

NMR (CDCl$_3$, δ): Ca. 1–3–1.6 (8H, broad), Ca. 1.7–2.1 (4H, m), 3.00 (2H, t, J=7.6Hz), 4.34 (2H, t, J=7.2Hz), 6.90 (1H, d, J=9.6Hz), 6.95 (1H, t, J=6.9Hz), 7.11 (1H, d, J=9.6Hz), 7.35 (1H, t, J=7.9Hz), 7.44–7.48 (3H, m), 7.58–7.63 (2H, m), 8.00 (1H, d, J=8.9Hz), 8.55 (1H, d, J=6.9Hz)

EXAMPLE 39

3-[2-{9-(1H-Tetrazol-5-yl)nonyl}-3-oxo-2,3-dihydropyridazin-6-yl]-2-phenylpyrazolo[1,5-a]pyridine mp: 155° to 156° C.

IR (Nujol): 1635, 1560, 1535, 1490 cm$^{-1}$

NMR (CDCl$_3$, δ): 1.13–1.60 (10H, m), 1.65–2.07 (4H, m), 2.99 (2H, t, J=7.8Hz), 4.34 (2H, t, J=7.5Hz), 6.95 (1H, m), 6.96 (1H, d, J=9.6Hz), 7.13 (1H, d, J=9.6Hz), 7.35 (1H, m), 7.43–7.53 (3H, m), 7.53–7.68 (2H, m), 8.00 (1H, d, J=8.9Hz), 8.55 (1H, d, J=7.0Hz), 15.9 (1H, broad s)

EXAMPLE 40

3-[2-{10-(1H-Tetrazol-5-yl)decyl}-3-oxo-2,3-dihydropyridazin-6-yl]-2-phenylpyrazolo[1,5-a]pyridine mp: 135° to 136° C.

IR (Nujol): 1635, 1560, 1535, 1490 cm$^{-1}$

NMR (CDCl$_3$, δ): 1.13–1.57 (12H, m), 1.67–2.07 (4H, m), 2.97 (2H, t, J=7.6Hz), 4.33 (2H, t, J=7.4 Hz), 6.94 (1H, d, J=9.6Hz), 6.98 (1H, m), 7.11 (1H, d, J=9.6Hz), 7.35 (1H, m), 7.40–7.52 (3H, m), 7.52–7.67 (2H, m), 8.00 (1H, d, J=8.9Hz), 8.56 (1H, d, J=7.0Hz)

EXAMPLE 41

3-[2-{12-(1H-Tetrazol-5-yl)dodecyl}-3-oxo-2,3-dihydropyridazin-6-yl]-2-phenylpyrazolo[1,5-a]pyridine mp: 134° to 135° C.

IR (Nujol): 1635, 1560, 1535, 1490 cm$^{-1}$

NMR (CDCl$_3$, δ): 1.10–1.55 (6H, m), 1.73–2.10 (4H, m), 2.96 (2H, t, J=7.5Hz), 4.33 (2H, t, J=7.3Hz), 6.91 (1H, d, J=9.6Hz), 6.96 (1H, m), 7.09 (1H, d, J=9.6Hz), 7.35 (1H, m), 7.40–7.53 (3H, m), 7.53–7.70 (2H, m), 8.00 (1H, d, J=8.9Hz), 8.57 (1H, d, J=7.0Hz)

The following compounds (Examples 42 to 67) were obtained according to a similar manner to that of Example 1.

EXAMPLE 42

3-[2-(2-Aminoethyl)-3-oxo-2,3-dihydropyridazin-6-yl]-2-phenylpyrazolo[1,5-a]pyridine IR (Nujol): 3380, 3300, 1660, 1630 cm$^{-1}$

EXAMPLE 43

3-[2-{2-(Ethoxycarbonylmethylamino)ethyl}-3-oxo-2,3-dihydropyridazin-6-yl]-2-phenylpyrazolo[1,5-a]pyridine IR (Nujol): 2750, 2170, 2120, 2430, 1760, 1650, 1630 cm$^{-1}$

EXAMPLE 44

3-[2-{2-(Carboxymethylamino)ethyl}-3-oxo-2,3-dihydropyridazin-6-yl]-2-phenylpyrazolo[1,5-a]pyridine IR (Nujol): 3400, 1650, 1600 cm$^{-1}$

EXAMPLE 45

3-[2-{2-{2-Hydroxy-3-(1-naphthyloxy)propylamino}ethyl}-3-oxo-2,3-dihydropyridazin-6-yl]-2-phenylpyrazolo-[1,5-a]pyridine NMR (CDCl$_3$, δ): 2.0–3.0 (2H, broad m), 2.9–3.1 (2H, m), 3.1–3.4 (2H, m), 4.0–4.3 (3H, m), 4.3–4.6 (2H, m), 6.7–6.8 (2H, m), 6.8–6.9 (1H, m), 6.98 (1H, d, J=10Hz), 7.0–7.5 (8H, m), 7.5–7.6 (2H, m), 7.7–7.8 (1H, m), 7.9–8.0 (1H, m), 8.1–8.2 (1H, m), 8.4–8.5 (1H, m)

EXAMPLE 46

3-[2-(4-Dimethylaminobutyl)-3-oxo-2,3-dihydropyridazin-6-yl]-2-phenylpyrazolo[1,5-a]pyridine hydrochloride IR (Nujol): 3100, 3050, 2400, 1660, 1630 cm$^{-1}$

EXAMPLE 47

3-[2-{2-{4-(2-Hydroxyethyl)piperazin-1-yl}ethyl}-3-oxo-2,3-dihydropyridazin-6-yl]-2-phenylpyrazolo[1,5-a]pyridine dihydrochloride
IR (Nujol): 3400, 1660, 1590 cm$^{-1}$

EXAMPLE 48

3-[2-{2-{4-(2-Methoxyphenyl)piperazin-1-yl}ethyl}-3-oxo-2,3-dihydropyridazin-6-yl]-2-phenyl-pyrazolo[1,5-a]pyridine
IR (Nujol): 1680, 1585, 1525, 1500 cm$^{-1}$

EXAMPLE 49

3-[2-{2-(1H-Tetrazol-5-yl)ethyl}-3-oxo-2,3-dihydropyridazin-6-yl]-2-phenylpyrazolo[1,5-a]pyridine
IR (Nujol): 1660, 1585 cm$^{-1}$

EXAMPLE 50

3-[2-{3-(1H-Tetrazol-5-yl)propyl}-3-oxo-2,3-dihydropyridazin-6-yl]-2-phenylpyrazolo[1,5-a]pyridine
IR (Nujol): 1665, 1595 cm$^{-1}$

EXAMPLE 51

3-[2-{4-(1H-Tetrazol-5-yl)butyl}-3-oxo-2,3-dihydropyridazin-6-yl]-2-phenylpyrazolo[1,5-a]pyridine
IR (Nujol): 1635, 1565 cm$^{-1}$

EXAMPLE 52

3-(2-Vinyl-3-oxo-2,3-dihydropyridazin-6-yl)-2-phenylpyrazolo[1,5-a]pyridine
IR (Nujol): 1680, 1635, 1605 cm$^{-1}$

EXAMPLE 53

3-[2-(5-Cyanopentyl)-3-oxo-2,3-dihydropyridazin-6-yl]-2-phenylpyrazolo[1,5-a]pyridine
IR (Nujol): 2245 (weak), 1660, 1630 (shoulder), 1590 cm$^{-1}$

EXAMPLE 54

3-[2-(6-Cyanohexyl)-3-oxo-2,3-dihydropyridazin-6-yl]-2-phenylpyrazolo[1,5-a]pyridine
IR (Nujol): 2245 (weak), 1660, 1630, 1590 cm$^{-1}$

EXAMPLE 55

3-[2-(7-Cyanoheptyl)-3-oxo-2,3-dihydropyridazin-6-yl]-2-phenylpyrazolo[1,5-a]pyridine
IR (Nujol): 2250 (weak), 1660, 1630, 1590 cm$^{-1}$

EXAMPLE 56

3-[2-(8-Cyanooctyl)-3-oxo-2,3-dihydropyridazin-6-yl]-2-phenylpyrazolo[1,5-a]pyridine
IR (Nujol): 2230 (weak), 1650, 1580 cm$^{-1}$

EXAMPLE 57

3-[2-(9-Cyanononyl)-3-oxo-2,3-dihydropyridazin-6-yl]-2-phenylpyrazolo[1,5-a]pyridine
IR (Nujol): 2240, 1655, 1630, 1585, 1525 cm$^{-1}$

EXAMPLE 58

3-[2-(10-Cyanodecyl)-3-oxo-2,3-dihydropyridazin-6-yl]-2-phenylpyrazolo[1,5-a]pyridine
IR (Nujol): 2240, 1645, 1580, 1520 cm$^{-1}$

EXAMPLE 59

3-[2-(12-Cyanododecyl)-3-oxo-2,3-dihydropyridazin-6-yl]-2-phenylpyrazolo[1,5-a]pyridine
IR (Nujol): 2240, 1655, 1630, 1585, 1530 cm$^{-1}$

EXAMPLE 60

3-[2-{(1H-Tetrazol-5-yl)methyl}-3-oxo-2,3-dihydropyridazin-6-yl]-2-phenylpyrazolo[1,5-a]pyridine
IR (Nujol): 1650, 1580 cm$^{-1}$

EXAMPLE 61

3-[2-{5-(1H-Tetrazol-5-yl)pentyl}-3-oxo-2,3-dihydropyridazin-6-yl]-2-phenylpyrazolo[1,5-a]pyridine
IR (Nujol): 1635, 1560 cm$^{-1}$

EXAMPLE 62

3-[2-{6-(1H-Tetrazol-5-yl)hexyl}-3-oxo-2,3-dihydropyridazin-6-yl]-2-phenylpyrazolo[1,5-a]pyridine
IR (Nujol): 1640, 1560 cm$^{-1}$

EXAMPLE 63

3-[2-{7-(1H-Tetrazol-5-yl)heptyl}-3-oxo-2,3-dihydropyridazin-6-yl]-2-phenylpyrazolo[1,5-a]pyridine
IR (Nujol): 1650, 1580 cm$^{-1}$

EXAMPLE 64

3-[2-{8-(1H-Tetrazol-5-yl)octyl}-3-oxo-2,3-dihydropyridazin-6-yl]-2-phenylpyrazolo[1,5-a]pyridine
IR (Nujol): 1635, 1550–1565 (broad) cm$^{-1}$

EXAMPLE 65

3-[2-{9-(1H-Tetrazol-5-yl)nonyl}-3-oxo-2,3-dihydropyridazin-6-yl]-2-phenylpyrazolo[1,5-a]pyridine
IR (Nujol): 1635, 1560, 1535, 1490 cm$^{-1}$

EXAMPLE 66

3-[2-{10-(1H-Tetrazol-5-yl)decyl}-3-oxo-2,3-dihydropyridazin-6-yl]-2-phenylpyrazolo[1,5-a]pyridine
IR (Nujol): 1635, 1560, 1535, 1490 cm$^{-1}$

EXAMPLE 67

3-[2-{12-(1H-Tetrazol-5-yl)dodecyl}-3-oxo-2,3-dihydropyridazin-6-yl]-2-phenylpyrazolo[1,5-a]pyridine
IR (Nujol): 1635, 1560, 1535, 1490 cm$^{-1}$ The following compounds (Example 68 to 76) were obtained according to a similar manner to that of Example 18.

EXAMPLE 68

3-[2-(2-Morpholinoethyl)-3-oxo-2,3-dihydropyridazin-6-yl]-2-phenylpyrazolo[1,5-a]pyridine hydrochloride
IR (Nujol): 2325, 1670, 1590 cm$^{-1}$

EXAMPLE 69

3-[2-(2-Piperidinoethyl)-3-oxo-2,3-dihydropyridazin-6-yl]-2-phenylpyrazolo[1,5-a]pyridine hydrochloride
IR (Nujol): 2495, 1660, 1595 cm$^{-1}$

EXAMPLE 70

3-[2-(2-Dimethylaminoethyl)-3-oxo-2,3-dihydropyridazin-6-yl]-2-phenylpyrazolo[1,5-a]pyridine hydrochloride
IR (Nujol): 3520, 3450, 2600, 2370, 1640, 1570 cm$^{-1}$

EXAMPLE 71

3-[2-(3-Dimethylaminopropyl)-3-oxo-2,3-dihydropyridazin-6-yl]-2-phenylpyrazolo[1,5-a]pyridine hydrochloride
IR (Nujol): 2400, 1655, 1590 cm$^{-1}$

EXAMPLE 72

3-[2-(2-Phthalimidoethyl)-3-oxo-2,3-dihydropyridazin-6-yl]-2-phenylpyrazolo[1,5-a]pyridine IR (Nujol): 1760, 1710, 1660, 1630 cm$^{-1}$

EXAMPLE 73

3-[2-(2-Aminoethyl)-3-oxo-2,3-dihydropyridazin-6-yl]-2-phenylpyrazolo[1,5-a]pyridine IR (Nujol): 3380, 3300, 1660, 1630 cm$^{-1}$

EXAMPLE 74

3-[2-{2-(Ethoxycarbonylmethylamino)ethyl}-3-oxo-2,3-dihydropyridazin-6-yl]-2-phenylpyrazolo[1,5-a]pyridine IR (Nujol): 2750, 2170, 2120, 2430, 1760, 1650, 1630 cm$^{-1}$

EXAMPLE 75

3-[2-{2-(Carboxymethylamino)ethyl}-3-oxo-2,3-dihydropyridazin-6-yl]-2-phenylpyrazolo[1,5-a]pyridine IR (Nujol): 3400, 1650, 1600 cm$^{-1}$

EXAMPLE 76

3-[2-{2-(2-Hydroxy-3-(1-naphthyloxy)propylamino}-ethyl}-3-oxo-2,3-dihydropyridazin-6-yl]-2-phenylpyrazolo[1,5-a]pyridine NMR (CDCl$_3$, δ): 2.0–3.0 (2H, broad m), 2.9–3.1 (2H, m), 3.1–3.4 (2H, m), 4.0–4.3 (3H, m), 4.3–4.6 (2H, m), 6.7–6.8 (2H, m), 6.8–6.9 (1H, m), 6.98 (1H, d, J=10Hz), 7.0–7.5 (8H, m), 7.5–7.6 (2H, m), 7.7–7.8 (1H, m), 7.9–8.0 (1H, m), 8.1–8.2 (1H, m), 8.4–8.5 (1H, m)

EXAMPLE 77

Thionyl chloride (145 mg) was added dropwise to a stirred mixture of 3-(2-phenylpyrazolo[1,5-a]pyridin-3-yl)acrylic acid (trans isomer) (270 mg) and N,N-dimethylformamide (1 drop) in methylene chloride (1.5 ml) under ice-cooling. After being stirred at room temperature for 2 hours and 50 minutes, the solvent was evaporated in vacuo to give acid chloride derivative. The above acid chloride derivative was added by portions to a stirred mixture of (R)-2-(methoxycarbonylmethyl)-piperidine hydrochloride (237 mg) and triethylamine (340 μl) in methylene chloride (1.5 ml) at −10° C.

The reaction mixture was stirred at room temperature overnight and then poured into ice-water (10 ml). The mixture was extracted with methylene chloride (20 ml×2). The combined extracts were washed with 0.1N HCl (10 ml), 10% aq K$_2$CO$_3$ (10 ml) and brine (10 ml), dried over sodium sulfate and evaporated in vacuo to give crude material, which was purified by column chromatography on silica gel (10 g) with a mixture of ethyl acetate and methylene chloride (1:10) as an eluent to give (2R)-1-[3-(2-phenylpyrazolo[1,5-a]pyridin-3-yl)acryloyl]-2-(methoxycarbonylmethyl)piperidine (trans isomer) (330 mg) as an oil.

$[\alpha]_D^{19}$= +65.11° (C=18, MeOH)

IR (Film): 1730, 1635, 1590, 1515 cm$^{-1}$

NMR (CDCl$_3$, δ): 1.33–1.77 (7H, m), 2.61 (1H, dd, J=14.7 and 7.1Hz), 2.76 (1H, brd s), 3.66 (3H, s), 4.76 (1H, brd s), 6.90 (1H, td, J=6.9 and 1.2Hz), 7.35 (1H, t, J=7.4Hz), 7.43–7.55 (3H, m), 7.72 (1H, dd, J=7.7 and 1.7Hz), 7.95 (1H, d, J=15.5Hz), 8.53 (1H, d, J=6.9Hz)

MS: m/e 403 (M+)

EXAMPLE 78

(2RS)-1-[3-(2-Phenylpyrazolo[1,5-a]pyridin-3-yl)acryloyl]-2-(methoxycarbonylmethyl)piperidine (trans isomer) was obtained according to a similar manner to that of Example 77

IR (Film): 1730, 1635, 1590, 1510 cm$^{-1}$

NMR spectrum was the same as that of the compound of Example 77.

EXAMPLE 79

A mixture of (2R)-1-[3-(2-phenylpyrazolo[1,5-a]pyridin-3-yl)acryloyl]-2-(methoxycarbonylmethyl)piperidine (trans isomer) (210 mg) and 1N sodium hydroxide solution (0.573 ml) in methanol (2.0 ml) was heated to reflux for 2 hours. Methanol was evaporated in vacuo and water (20 ml) was added to the residue. The solution was acidified with 1N hydrochloric acid and extracted with methylene chloride (10 ml×2). The combined extracts were washed with brine (10 ml), dried over sodium sulfate and evaporated in vacuo. The crude crystals were recrystallized from a mixture of ethyl acetate and diethyl ether to give colorless crystals of (2R)-1-[3-(2-phenylpyrazolo[1,5-a]pyridin-3-yl)acryloyl]-2-(carboxymethyl)piperidine (trans isomer) (152.7 mg).

mp: 165°–166° C.

$[\alpha]_D^{18}$= +72.75° (C=1.09, MeOH)

IR (Nujol): 1715, 1625, 1570, 1510 cm$^{-1}$

NMR (CDCl$_3$, δ): 1.36–1.82 (7H, m), 2.57 (1H, dd, J=15.1 and 6.4Hz), 2.67–3.25 (2H, m), 4.69 (1H, brd s), 6.40–7.34 (2H, m), 7.37–7.51 (4H, m), 7.65–7.77 (3H, m), 7.89 (1H, d, J=15.5Hz), 8.44 (1H, brd s), 10.40 (1H, brd s)

Anal. Calcd. for C$_{23}$H$_{23}$N$_3$O$_3$: C 70.93, H 5.95, N 10.79 Found: C 70.81, H 5.97, N 10.66

EXAMPLE 80

(2RS)-1-[3-(2-Phenylpyrazolo[1,5-a]pyridin-3-yl)-acryloyl]-2-(carboxymethyl)piperidine (trans isomer) was obtained according to a similar manner to that of Example 79.

mp: 132°–134° C.

IR (Nujol): 1705, 1625, 1560, 1505 cm$^{-1}$

NMR spectrum was the same as that of the compound of Example 79.

EXAMPLE 81

A solution of dimethyl sulfoxide (202 mg) in methylene chloride (1.0 ml) was added dropwise to a solution of oxalyl dichloride (247 mg) in methylene chloride (10 ml) over 5 minutes at −78° C. After 10 minutes, a solution of (2R)-1-[3-(2-phenylpyrazolo[1,5-a]pyridin-3-yl)acryloyl]-2-(2-hydroxyethyl)piperidine (trans isomer) (364 mg) in methylene chloride (3.4 mg) was added dropwise over 10 minutes at −78° C. The solution was stirred at −78° C. for 20 minutes and at −45° C. for 1 hour. Triethylamine (986 μl) was added to the solution and the mixture was stirred at −20°~0° C. for 20 minutes. Saturated ammonium chloride solution (20 ml) was added to the reaction mixture and the mixture was extracted with methylene chloride (10 ml×2). The combined extracts were washed with brine (10 ml), dried over magnesium sulfate and evaporated in vacuo. The crude material was purified by column chromatography on silica gel (10 g) with a mixture of methylene chloride and ethyl acetate (10:1) as an eluent to give (2R)-1-[3-(2-phenylpyrazolo-[1,5-a]pyridin-3-yl)acryloyl]-2-(formylmethyl)piperidine (trans isomer) (139.0 mg) as an oil.

$[\alpha]_D^{17}$= +35.41° (C=1.44, MeOH)

IR (Film): 1720, 1640, 1590, 1520 cm$^{-1}$

NMR (CDCl$_3$, δ): 1.05–2.10 (8H, m), 2.22–3.12 (3H, m), 6.50–6.93 (2H, m), 7.05–7.54 (4H, m), 7.67–7.81 (3H, m), 7.93 (1H, d, J=15.4Hz), 8.45–8.53 (1H, m), 9.68–9.75 (1H, m)

What we claim is:

1. A method for the treatment of pancreatitis, which comprises administering an effective amount of a pyrazolopyridine compound of the following formula:

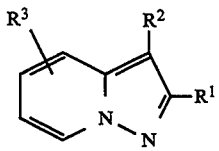

wherein

R¹ is lower alkyl, aryl which may have one or more substituent(s) selected from the group consisting of halogen, lower alkoxy, nitro, amino, protected amino, (C₁–C₄)alkylamino and di(C₁–C₄)alkylamino, or a heterocyclic group selected from the group consisting of saturated or unsaturated 3- to 8-membered heteromonocyclic groups containing from 1 to 4 nitrogen atom(s), saturated or unsaturated condensed heterocyclic groups containing from 1 to 4 nitrogen atom(s), saturated or unsaturated 3- to 8-membered heteromonocyclic groups containing from 1 to 2 oxygen atom(s) and from 1 to 3 nitrogen atom(s), unsaturated condensed heterocyclic groups containing from 1 to 2 oxygen atom(s) and from 1 to 3 nitrogen atom(s), saturated or unsaturated 3- to 8-membered heteromonocyclic groups containing from 1 to 2 sulphur atom(s) and from 1 to 3 nitrogen atom(s), unsaturated condensed heterocyclic groups containing from 1 to 2 sulphur atom(s) and from 1 to 3 nitrogen atom(s), unsaturated 3- to 8-membered heteromonocyclic groups containing an oxygen atom, unsaturated 3- to 8-membered heteromonocyclic groups containing an oxygen atom and from 1 to 2 sulphur atom(s), unsaturated condensed heterocyclic groups containing from 1 to 2 sulphur atom(s) and unsaturated condensed heterocyclic groups containing an oxygen atom and from 1 to 2 sulphur atoms, R² is a group of the formula

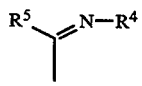

wherein R⁴ is protected amino or hydroxy and R⁵ is hydrogen or lower alkyl;

cyano;

a group of the formula —A—R⁶, wherein R⁶ is an acyl group, and A is lower aliphatic hydrocarbon group which may have one or more suitable halogen substituent(s);

amidated carboxy;

an unsaturated heterocyclic group selected from the group consisting of unsaturated 3- to 8-membered heteromonocyclic groups containing from 1 to 4 nitrogen atom(s), unsaturated condensed heterocyclic groups containing from 1 to 4 nitrogen atom(s), unsaturated 3- to 8-membered heteromonocyclic groups containing from 1 to 2 oxygen atom(s) and from 1 to 3 nitrogen atom(s), unsaturated condensed heterocyclic groups containing from 1 to 2 oxygen atom(s) and from 1 to 3 nitrogen atom(s), unsaturated 3- to 8-membered heteromonocyclic groups containing from 1 to 2 sulphur atom(s) and from 1 to 3 nitrogen atom(s), unsaturated condensed heterocyclic groups containing from 1 to 2 sulphur atom(s) and from 1 to 3 nitrogen atom(s), unsaturated 3- to 8-membered heteromonocyclic groups containing from 1 to 2 sulphur atom(s), unsaturated 3- to 8-membered heteromonocyclic groups containing an oxygen atom, unsaturated 3-8-membered heteromonocyclic groups containing an oxygen atom and from 1 to 2 sulphur atom(s), unsaturated condensed heterocyclic groups containing from 1 to 2 sulphur atom(s) and unsaturated condensed heterocyclic groups containing an oxygen atom and from 1 to 2 sulphur atoms, which may have one or more substituent(s) selected from the group consisting of carboxy(lower)alkenyl; amino; di(lower)alkylamino; halogen; lower alkoxy; oxo; hydroxy; cyano; acyl; amino(lower)alkyl; lower alkylamino(lower)alkyl; carboxy(lower)alkylamino(lower)alkyl; protected carboxy(lower)alkylamino(lower)alkyl; lower alkylamino(lower)alkyl having hydroxy and naphthyloxy; protected amino(lower)alkyl; cyano(lower)alkyl; cyano(higher)alkyl; lower alkyl which may have one or more suitable substituent(s) selected from the group consisting of hydroxy, halogen, lower alkoxy and acyl; higher alkyl having an unsaturated 3- to 8-membered heteromonocyclic group containing from 1 to 4 nitrogen atom(s); phenyl(lower)alkyl; lower alkenyl; lower alkyl having a heterocyclic group selected from the group consisting of a saturated or unsaturated 3- to 8-membered heteromonocyclic group containing from 1 to 4 nitrogen atom(s), a saturated 3- to 8-membered heteromonocyclic group containing from 1 to 2 oxygen atom(s) and from 1 to 3 nitrogen atom(s), and saturated 3 to 8-membered heteromonocyclic group containing from 1 to 2 oxygen atom(s), in which said heterocyclic group may have from 1 to 3 suitable substituent(s) selected from the group consisting of hydroxy(lower)alkyl and phenyl which may have a lower alkoxy substituent; and dihydrochromenyl which may have one or more substituent(s) selected from the group consisting of lower alkyl, hydroxy and cyano; or amino or protected amino; and R³ is hydrogen, lower alkyl, lower alkoxy or halogen;

or a pharmaceutically acceptable salt thereof, to a human being having pancreatitis or an animal having pancreatitis in need thereof.

2. The method of claim 1, wherein said pyrazolopyridine compound has the following formula:

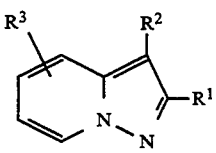

wherein

R¹ is lower alkyl, phenyl which may have one or more suitable substituent(s) selected from the group consisting of halogen, lower alkoxy, nitro, amino, protected amino, (C₁–C₄)alkylamino and di(C$_1$–C$_4$)alkylamino, or an unsaturated 3- to 8-membered heteromonocyclic group containing 1 to 4 nitrogen atom(s), R$^2$ is a group of the formula

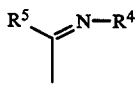

wherein R$^4$ is protected amino or hydroxy and R$^5$ is hydrogen or lower alkyl;

cyano;

a group of the formula —A—R$^6$, wherein R$^6$ is an acyl group, and A is lower alkyl, lower alkenyl or lower alkynyl, each of which may have one or more halogen substituent(s);

amidated carboxy;

an unsaturated 3- to 8-membered heteromonocyclic group containing 1 to 4 nitrogen atom(s) or an unsaturated condensed heterocyclic group containing 1 to 2 sulfur atom(s) and 1 to 3 nitrogen atom(s), each of which may have one or more substituent(s) selected from the group consisting of carboxy(lower)alkenyl; amino; di(lower)alkylamino; halogen; lower alkoxy; oxo; hydroxy; cyano; acyl; amino(lower)alkyl; lower alkylamino(lower)alkyl; carboxy(lower)alkylamino(lower)alkyl; protected carboxy(lower)alkylamino(lower)alkyl; lower alkylamino(lower)alkyl having hydroxy and naphthyloxy; protected amino(lower)alkyl; cyano(lower)alkyl; cyano(higher)alkyl; lower alkyl which may have one or more suitable substituent(s) selected from the group consisting of hydroxy, halogen, lower alkoxy and acyl; higher alkyl having an unsaturated 3- to 8-membered heteromonocyclic group containing from 1 to 4 nitrogen atom(s); phenyl(lower)alkyl; lower alkenyl; lower alkyl having a heterocyclic group selected from the group consisting of a saturated or unsaturated 3- to 8-membered heteromonocyclic group containing from 1 to 4 nitrogen atom(s), a saturated 3- to 8-membered heteromonocyclic group containing from 1 to 2 oxygen atom(s) and from 1 to 3 nitrogen atom(s), and saturated 3 to 8-membered heteromonocyclic group containing from 1 to 2 oxygen atom(s), in which said heterocyclic group may have from 1 to 3 suitable substituent(s) selected from the group consisting of hydroxy(lower)alkyl and phenyl which may have a lower alkoxy substituent; and dihydrochromenyl which may have one or more substituent(s) selected from the group consisting of lower alkyl, hydroxy and cyano;

amino or protected amino; and

R$^3$ is hydrogen, lower alkyl, lower alkoxy or halogen, or a pharmaceutically acceptable salt thereof.

3. The method of claim 2, wherein said pyrazolopyridine compound has the following formula:

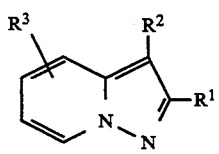

wherein

R$^1$ is phenyl which may have 1 to 3 substituent(s) selected from the group consisting of halogen, lower alkoxy, nitro, amino, lower alkanoylamino, lower alkoxycarbonylamino, lower alkanesulfonylamino, lower alkylamino and di(lower)alkylamino, R$^2$ is a group of the formula —A—R$^6$, wherein R$^6$ is lower alkanoyl, carboxy or protected carboxy, and A is lower alkyl, lower alkenyl, lower alkenyl having one or more halogen substituent(s) or lower alkynyl; or an unsaturated 3- to 8-membered heteromonocyclic group containing 1 to 4 nitrogen atom(s) which may have 1 to 4 substituent(s) selected from the group consisting of lower alkyl; lower alkyl having hydroxy and halogen; hydroxy(lower)alkyl; lower alkoxy(lower)alkyl; carboxy(lower)alkyl; protected carboxy(lower)alkyl; amino(lower)alkyl; lower alkylamino(lower)alkyl; carboxy(lower)alkylamino(lower)alkyl; protected carboxy(lower)alkylamino(lower)alkyl; lower alkylamino(lower)alkyl having hydroxy and aryloxy; protected amino(lower)alkyl; cyano(lower)alkyl; cyano(higher)alkyl; lower alkyl having a heterocyclic group, in which said heterocyclic group may have one or more substituent(s); higher alkyl having a heterocyclic group, in which said heterocyclic group may have one or more substituent(s); ar(lower)alkyl; lower alkenyl; a heterocyclic group which may have one or more substituent(s); carboxy(lower)alkenyl; amino; di(lower)alkylamino; halogen; lower alkoxy; oxo; hydroxy; cyano; carboxy; protected carboxy and lower alkanoyl; and R$^3$ is hydrogen, or a pharmaceutically acceptable salt thereof.

4. The method of claim 3, wherein said pyrazolopyridine compound has the following formula:

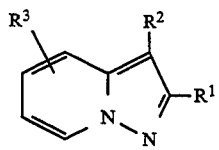

wherein

R$^1$ and R$^3$ are each as defined in claim 3, and

R$^2$ is a group of the formula —A—R$^6$, wherein R$^6$ is lower alkanoyl; carboxy; lower alkoxycarbonyl which may have N-containing heterocyclic group; N-(lower)alkylcarbamoyl; N-(higher)alkylcarbamoyl; N,N-di(lower)alkylcarbamoyl; N-lower alkyl-N-ar(lower)-alkylcarbamoyl; or a group of the formula —COR$_N$, wherein R$_N$ is a saturated 3- to 8-membered heteromonoyclic group containing 1 to 4 nitrogen atom(s); a saturated condensed heterocyclic group containing 1 to 4 nitrogen atom(s); or a saturated 3- to 8-membered heteromonocyclic group containing 1 to 2 oxygen atom(s) and 1 to 3 nitrogen atom(s), in which each of said heteromonocyclic groups and said saturated condensed heterocyclic group may have one or more substituent(s) selected from the group consisting of lower alkyl, hydroxy(lower)alkyl, lower alkoxy(lower)alkyl, acyloxy(lower)alkyl, acyl(lower)alkyl, carboxy and protected carboxy; and A is as defined in claim 3, or an unsaturated 3- to 8-membered heteromonocyclic group containing 1 to 4 nitrogen atom(s) which may have 1 to 4 substituent(s) selected from the group consisting of lower alkyl; lower alkyl having hydroxy and halogen; hydroxy(lower)alkyl; lower alkoxy(lower)alkyl; carboxy(lower)alkyl; protected carboxy(lower)alkyl; amino(lower)alkyl; lower alkylamino(lower)alkyl; carboxy(lower)alkylamino(lower)alkyl; protected carboxy(lower)alkylamino(lower)alkyl; lower alkylamino(lower)alkyl having hydroxy and aryloxy; protected amino(lower)alkyl; cyano(lower)alkyl; cyano(higher)alkyl; lower alkyl having a heterocyclic group, in which said heterocyclic group may have one or more substituent(s); higher alkyl having a heterocyclic group, in which said heterocyclic group may have one or more suitable substituent(s); ar(lower)alkyl; lower alkenyl; a heterocyclic group which may have one or more substituent(s); carboxy(lower)alkenyl; amino; di(lower)alkylamino; halogen; lower alkoxy; oxo; hydroxy; cyano; carboxy; protected carboxy and lower alkanoyl; or a pharmaceutically acceptable salt thereof.

5. The method of claim 4, wherein said pyrazolopyridine compound has the following formula:

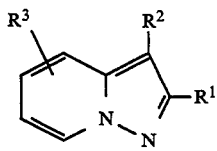

wherein $R^1$ and $R^3$ are each as defined in claim 4, and $R^2$ is a group of the formula —A—COR$_N$, wherein R$_N$ is piperidino, pyrrolidin-1-yl, perhydroazepin-1-yl, piperazin-1-yl, morpholino, 7-azabicyclo[2.2.2]heptan-7-yl or 3-azabicyclo[3.2.2]nonan-3-yl, each of which may have 1 to 4 substituent(s) selected from the group consisting of lower alkyl, hydroxy(lower)alkyl, lower alkoxy(lower)alkyl, lower alkanoyloxy(lower)alkyl, lower alkanoyl(lower)alkyl, carboxy(lower)alkyl, lower alkoxycarbonyl(lower)alkyl, lower alkoxycarbonyl and carboxy, and A is as defined in claim 4;

pyridazinyl, dihydropyridazinyl, tetrahydropyridazinyl, pyrimidinyl, dihydropyrimidinyl, pyridyl, dihydropyridyl, tetrahydropyridyl, pyrazolyl or imidazothiadiazolyl, each of which may have 1 to 4 substituent(s) selected from the group consisting of lower alkyl; lower alkyl having hydroxy and halogen; hydroxy(lower)alkyl; lower alkoxy(lower)alkyl; carboxy(lower)alkyl; protected carboxy(lower)alkyl; amino(lower)alkyl; lower alkylamino(lower)alkyl; carboxy(lower)alkylamino(lower)alkyl; protected carboxy(lower)alkylamino(lower)alkyl; lower alkylamino(lower)alkyl having hydroxy and aryloxy; protected amino(lower)alkyl; cyano(lower)alkyl; cyano(higher)alkyl; lower alkyl having a heterocyclic group, in which said heterocyclic group may have one or more substituent(s); higher alkyl having a heterocyclic group, in which said heterocyclic group may have one or more substituent(s); ar(lower)alkyl; lower alkenyl; a heterocyclic group which may have one or more substituent(s); carboxy(lower)alkenyl; amino; di(lower)alkylamino; halogen; lower alkoxy; oxo; hydroxy; cyano; carboxy; protected carboxy and lower alkanoyl;

or a pharmaceutically acceptable salt thereof.

6. The method of claim 5, wherein said pyrazolopyridine compound has the following formula:

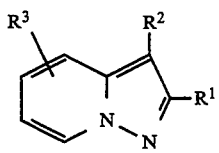

wherein $R^1$ and $R^3$ are each as defined in claim 5, and $R^2$ is a group of the formula —A—COR$_N$, wherein R$_N$ is piperidino which may have 1 to 4 suitable substituent(s) selected from the group consisting of lower alkyl, hydroxy(lower)alkyl, lower alkoxy(lower)alkyl, lower alkanoyloxy(lower)alkyl, lower alkanoyl(lower)alkyl, carboxy(lower)alkyl, lower alkoxycarbonyl(lower)alkyl, lower alkoxycarbonyl and carboxy, and A is as defined in claim 5, or dihydropyridazinyl which may have 1 to 4 substituent(s) selected from the group consisting of lower alkyl; lower alkyl having hydroxy and halogen; hydroxy(lower)alkyl; lower alkoxy(lower)alkyl; carboxy(lower)alkyl; protected carboxy(lower)alkyl; amino(lower)alkyl; lower alkylamino(lower)alkyl; carboxy(lower)alkylamino(lower)alkyl; protected carboxy(lower)alkylamino(lower)alkyl; lower alkylamino(lower)alkyl having hydroxy and aryloxy; protected amino(lower)alkyl; cyano(lower)alkyl; cyano(higher)alkyl; lower alkyl having a heterocyclic group, in which said heterocyclic group may have one or more substituent(s); higher alkyl having a heterocyclic group, in which said heterocyclic group may have one or more substituent(s); ar(lower)alkyl; lower alkenyl; a heterocyclic group which may have one or more substituent(s); carboxy(lower)alkenyl; amino; di(lower)alkylamino; halogen; lower alkoxy; oxo; hydroxy; cyano; carboxy; protected carboxy and lower alkanoyl;

or a pharmaceutically acceptable salt thereof.

7. The method of claim 6, wherein said pyrazolopyridine compound has the following formula:

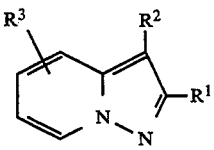

wherein $R^1$ is phenyl, $R^2$ is a group of the formula —A—COR$_N$, wherein R$_N$ is piperidino which may have hydroxy(lower)alkyl or carboxy(lower)alkyl, and A is lower alkenyl, or dihydropyridazinyl which may have carboxy(lower)alkyl and oxo;

$R^3$ is hydrogen; or a pharmaceutically acceptable salt thereof.

8. The method of claim 1, wherein said condensed heterocyclic groups are selected from the group consisting of indolyl, isoindolyl, indolizinyl, benzimidazoyl, quinolyl, isoquinolyl, indazolyl, benzotriazolyl, 7-azabicyclo[2.2.1]heptan-7-yl, 3-azabicyclo[3.2.2]nonan-3-yl, benzoxazolyl, benzoxadiazolyl, benzothiazolyl, benzothiadiazolyl, benzothienyl, benzodithiinyl, and benzoxathiinyl.

9. The method of claim 8, wherein $R^1$ is a heterocyclic group selected from the group consisting of azepinyl, pyrrolyl, pyrrolinyl, imidazolyl, pyrazolyl, pyridyl, pyridyl N-oxide, dihydropyridyl, pyrimidinyl, pyrazinyl, pyridazinyl, triazolyl, tetrazolyl, perhydroazepinyl, pyrrolidinyl, imidazolidinyl, piperidino, piperazinyl, oxazolyl, isoxazolyl, oxadiazolyl, morpholinyl, sydnonyl, thiazolyl, isothiazolyl, thiadiazolyl, dihydrothiazinyl, thiazolidinyl, furyl, dihydrooxathiinyl, benzothienyl and benzodithiinyl.

10. The method of claim 9, wherein $R^2$ is a heterocyclic group selected from the group consisting of azepinyl, pyrrolyl, pyrrolinyl, imidazolyl, pyrazolyl, pyridyl, pyridyl N-oxide, dihydropyridyl, pyrimidinyl, pyrazinyl, pyridazinyl, triazolyl, tetrazolyl, perhydroazepinyl, pyrrolidinyl, imidazolidinyl, piperidino, piperazinyl, oxazolyl, isoxazolyl, oxadiazolyl, morpholinyl, sydnonyl, thiazolyl, isothiazolyl, thiadiazolyl, dihydrothiazinyl, thiazolidinyl, furyl, dihydrooxathiinyl, benzothienyl and benzodithiinyl.

11. The method of claim 9, wherein $R^1$ is a heterocyclic group selected from the group consisting of piperidino which may have 1 to 4 substituent(s) selected from the group consisting of ($C_1$–$C_4$)alkyl, hydroxy($C_1$–$C_4$)alkyl, ($C_1$–$C_4$)alkoxy($C_1$–$C_4$)alkyl, ($C_1$–$C_4$)alkanoyloxy($C_1$–$C_4$)alkyl, ($C_1$–$C_4$)alkoxycarbonyl, carboxy, ($C_1$–$C_4$)alkanoyl($C_1$–$C_4$)alkyl, carboxy($C_1$–$C_4$)alkyl and ($C_1$–$C_4$)alkoxycarbonyl($C_1$–$C_4$)alkyl; pyrrolidin-1-yl which may have a ($C_1$–$C_4$)alkoxy($C_1$–$C_4$)alkyl substituent; perhydroazepin-1-yl; piperazin-1-yl which may have a ($C_1$–$C_4$)alkyl substituent; and morpholino.

12. The method of claim 8, wherein $R^1$ is 7-azabicyclo[2.2.1]heptan-7-yl or 3-azabicyclo[3.2.2]nonan-3-yl.

13. The method of claim 1, wherein $R^1$ is an aryl group selected from the group consisting of phenyl, naphthyl, indenyl and anthryl.

14. The method of claim 13, wherein said aryl group is phenyl.

15. The method of claim 13, wherein said aryl group may have one or more substituent(s) selected from the group consisting of ($C_1$–$C_4$)alkoxy, ($C_1$–$C_4$)alkanoylamino, ($C_1$–$C_4$)alkoxycarbonylamino and ($C_1$–$C_4$)alkanesulfonylamino.

* * * * *